US011446378B2

(12) United States Patent
Vermeer

(10) Patent No.: US 11,446,378 B2
(45) Date of Patent: Sep. 20, 2022

(54) INHIBITORS OF EPHRIN B1 FOR TUMOR TREATMENT

(71) Applicant: SANFORD HEALTH, Sioux Falls, SD (US)

(72) Inventor: Paola Vermeer, Sioux Falls, SD (US)

(73) Assignee: Sanford Health, Sioux Falls, SD (US)

( * ) Notice: Subject to any disclaimer, the term of this patent is extended or adjusted under 35 U.S.C. 154(b) by 0 days.

(21) Appl. No.: 16/482,048

(22) PCT Filed: Feb. 23, 2018

(86) PCT No.: PCT/US2018/019450
§ 371 (c)(1),
(2) Date: Jul. 30, 2019

(87) PCT Pub. No.: WO2018/156915
PCT Pub. Date: Aug. 30, 2018

(65) Prior Publication Data
US 2019/0365893 A1    Dec. 5, 2019

Related U.S. Application Data

(60) Provisional application No. 62/462,825, filed on Feb. 23, 2017, provisional application No. 62/548,264, filed on Aug. 21, 2017, provisional application No. 62/616,376, filed on Jan. 11, 2018.

(51) Int. Cl.
| *A61K 39/395* | (2006.01) |
| *A61K 31/506* | (2006.01) |
| *C07K 16/28* | (2006.01) |
| *C07K 16/40* | (2006.01) |
| *C12N 15/113* | (2010.01) |
| *G01N 33/50* | (2006.01) |

(52) U.S. Cl.
CPC ...... *A61K 39/39558* (2013.01); *A61K 31/506* (2013.01); *C07K 16/28* (2013.01); *C07K 16/40* (2013.01); *C12N 15/1138* (2013.01); *G01N 33/5011* (2013.01); *C07K 2317/76* (2013.01)

(58) Field of Classification Search
CPC .. C07K 16/28; C07K 16/40; A61K 39/39558; C12N 15/1138
See application file for complete search history.

(56) References Cited

U.S. PATENT DOCUMENTS

2006/0121042 A1* 6/2006 Dall'Acqua ............ A61P 35/04
424/155.1

FOREIGN PATENT DOCUMENTS

| WO | 1999/17796 | 4/1999 |
| WO | 2012/031008 | 3/2012 |
| WO | 2012/135844 | 10/2012 |
| WO | 2017/043370 | 3/2017 |

OTHER PUBLICATIONS

Almagro & Fransson, Huamnization of antibodies, Frontiers in Bioscience 2008; 13: 1619-1633, Publication Date: Jan. 1, 2008 (Year : 2008).*
Rudikoff et al., Single amino acid substitution altering antigen-binding specificity, Proc Natl Acad Sci USA 1982, 79(6) 1979-1983, Publication Year:1982 (Year: 1982).*
Riemer et al. Matchina of trastuzumab (Herceptin®) epitope mimics onto the surface of Her-2/neu—a new method of epitope definition, Mol Immunol, 2005 42(9): 1121-1124, Publication Date: Jan. 8, 2005 (Year: 2005).*
Colbert et al., EphrinBI: novel microtubule associated protein whose expression affects taxane sensitivity, Oncotarget, 20, 6(2):953-968, Publication Date: Nov. 26, 2014 (Year: 2014).*
EphrinB1 GeneCard: https://www.genecards.org/cgi-bin/carddisp.pl?gene=EFNB1 (Year: 2021).*
Grainger DW, Controlled-release and local delivery of therapeutic antibodies, Expert Opinion on Biological Therapy, 2004, 4(7): 1029-1044, Publication Date: Feb. 23, 2005 (Year: 2005).*
Vermeer et al., Targeting ERBB Receptors Shifts Their Partners and Triggers Persistent ERK Signaling through a Novel ERBB/EFNB1 Complex, Cancer Research, 73(18), 5787-5797, Publication Date: Jun. 28, 2013 (Year: 2013).*
The International Search Report (ISR) with Written Opinion for PCT/US2018/019450 dated Jun. 5, 2018, pp. 1-24.
Steinbichler, Teresa Bernadette et al. "The role of exosomes in cancer metastasis" Seminars in Cancer Biology (2017) vol. 44, pp. 170-181.
Record, Michel et al. "Exosomes as intercellular signalosomes and pharmacological effectors" Biochemical Pharmacology (2011) vol. 81, pp. 1171-1182.
Orikawa, Yuki et al. "Z-360, a novel therapeutic agent for pancreatic cancer, prevents up-regulation of ephrin B 1 gene expression and phosphorylation of NR2B via suppression of interleukin-1 β production in a cancer-induced pain model in mice" Molecular Pain (2010) vol. 6(72), pp. 1-11.
Alberto, Bosque et al. "Comparative proteomics of exosomes secreted .by tu moral Jurkat T cells and normal human T cell blasts unravels a potential tumorigenic role for valosin-containing protein" Database Biosis [Online] Biosciences Information Service (May 2016) XP002780889 Database accession No. PREV201600621211 abstract.
Ostrowski, Matias et al. "Rab27a and Rab27b control different steps of the exosome secretion pathway" Nature Cell Biology (2010) vol. 12(1), pp. 19-30.
Vermeer, Paola D. et al. "EphrinB1 is a novel microtubule associated protein whose expression may predict sensitivity to taxane" American Association for Cancer Research (2015) vol. 75(Suppl. 15), p. 3787.

(Continued)

Primary Examiner — Peter J Reddig
Assistant Examiner — Cheng Lu
(74) Attorney, Agent, or Firm — McDonnell Boehnen Hulbert & Berghoff

(57) ABSTRACT

Disclosed herein are compositions and methods for tumor treatment involving administering to a subject having a tumor with an amount effective to limit tumor growth or metastasis of an ephrin B1 inhibitor, or a pharmaceutically acceptable salt thereof; and/or an inhibitor of tumor exosomal release, or a pharmaceutically acceptable salt thereof.

12 Claims, 8 Drawing Sheets

Specification includes a Sequence Listing.

(56) References Cited

OTHER PUBLICATIONS

Vermeer, Paola D. et al. "Erb82, Ephrin81, Src kinase and PTPN13 signaling complex regulates MAP kinase signaling in human cancers" American Association for Cancer Research (2012) vol. 72(Suppl. 8), pages LB-143.
Taylor, Hannah et al. "Ephs and ephrins" Current Biology (2017) vol. 27(3), pp. R90-R95.
Goldshmit, Yona et al. "Roles of Eph receptors and ephrins in the normal and damaged adult CNS" Brain Research Reviews (2006) vol. 52(2), pp. 327-345.
Albo, et al., "Neurogenesis in Colorectal Cancer Is a Marker of Aggressive Tumor Behavior and Poor Outcomes," Cancer 2011;117:4834-45.
Cole, et al., "Sympathetic nervous system regulation of the tumour microenvironment," Nature Reviews Cancer, Sep. 2015, 563-572.
Ding, et al., "Semaphorin 4F as a Critical Regulator of Neuro-Epithelial Interactions and a Biomarker of Aggressive Prostate Cancer," Clin Cancer Res. Nov. 15, 2013; 19(22): 6101-6111.
Horvathova, et al., "Sympathectomy reduces tumor weight and affects expression of tumor-related genes in melanoma tissue in the mouse," Stress, 2016 vol. 19, No. 5, 528-534.
Li, et al., "Neurotransmitter Substance P Mediates Pancreatic Cancer Perineural Invasion via NK-1R in Cancer Cells," Mol Cancer Res. 2012; 11(3); 294-302.
Lisabeth, et al., "Eph Receptor Signaling and Ephrins," Cold Spring Harb Perspect Biol. 2013. 5:a009159.
Olar, et al., "Biologic correlates and significance of axonogenesis in prostate cancer," Human Pathology (2014) 45, 1358-1364.
Partecke, et al., "Chronic stress increases experimental pancreatic cancer growth, reduces survival and can be antagonised by beta-adrenergic receptor blockade," Pancreatology 16 (2016) 423-433.
Rutledge, et al., "Spinal Cord Injuries and Nerve Dependence in Prostate Cancer," Trends in Cancer, Dec. 2017, vol. 3, No. 12: 812-815.
Yin, et al., "Enhanced expression of EphrinB1 is associated with lymph node metastasis and poor prognosis in breast cancer," Cancer Biomarkers, 13 (2013) 261-267.
Zahalka, et al., "Adrenergic nerves activate an angio-metabolic switch in prostate cancer," Science 358, 321-326 (Oct. 2017).
Zhang, et al., "Sympathetic and parasympathetic innervation in hepatocellular carcinoma," Neoplasma. 2017 64(6):840-846.
Bobrie, et al. "Rab27a Supports Exosome-Dependent and -Independent Mechanisms That Modify the Tumor Microenvironment and Can Promote Tumor Progression," Cancer Res (2012) 72 (19): 4920-4930.
Beckmann, et al., "Molecular Characterization of a family of ligands for eph-related tyrosine kinase receptors," EMBO Journal, (1994) vol. 13, pp. 3757-3762.
Spanos, et al., "The PDZ binding motif of human papillomavirus type 16 E 6 induces PTPN13 loss, which allows anchorage-independent growth and synergizes with Ras for invasive growth," Journal of Virology (2008) vol. 82, pp. 2493-2500.

* cited by examiner

INHIBITORS OF EPHRIN B1 FOR TUMOR TREATMENT

RELATED APPLICATIONS

This application is a U.S. national phase of International Application No. PCT/US2018/019450, filed on Feb. 23, 2018, which claims priority to U.S. Provisional Application No. 62/462,825, filed Feb. 23, 2017; U.S. Provisional Application No. 62/548,264, filed Aug. 21, 2017 and U.S. Provisional Application No. 62/616,376, filed Jan. 11, 2018, all of which are incorporated by reference herein in their entirety.

FEDERAL FUNDING STATEMENT

This invention was made with government support under grant number P20GM103548 awarded by the National Institute of Health. The government has certain rights in the invention.

BACKGROUND

Innervated tumors are more aggressive than less innervated one. For instance, in prostate cancer, recruitment of nerve fibers to cancer tissue is associated with higher tumor proliferative indices and a higher risk of recurrence and metastasis. Denervation studies in pre-clinical and genetically engineered mouse cancer models support a functional contribution of neural elements in disease progression. These studies strongly indicate that the nervous system is not a bystander but instead an active participant in carcinogenesis and cancer progression. However, a mechanistic understanding of how tumors obtain their neural elements remains unclear. Tumors may acquire innervation by growing within innervated tissues; in other words, neural elements are already present within the microenvironment and the tumor acquires them by default. However, the clinical findings that some tumors of the same tissue are more innervated than others indicate instead an active, tumor-initiated process, similar to neo-angiogenesis and lymphangiogenesis. The possibility that tumors invoke their own innervation, termed neo-neurogenesis, has not been extensively explored.

SUMMARY

In one aspect is provided a method for tumor treatment comprising administering to a subject having a tumor with an amount effective to limit tumor growth or metastasis of:
(a) an ephrin B1 inhibitor, or a pharmaceutically acceptable salt thereof; and/or
(b) an inhibitor of tumor exosomal release, or a pharmaceutically acceptable salt thereof.

In one embodiment, the method limits tumor innervation. In another embodiment, the method comprises administering to the subject an amount effective of an ephrin B1 inhibitor, wherein the ephrin B1 inhibitor is selected from the group consisting ephrin B1-specific antibodies, aptamers, small interfering RNAs, small internally segmented interfering RNAs, short hairpin RNAs, microRNAs, and/or antisense oligonucleotides. In a specific embodiment, the ephrin B1 inhibitor comprises ephrin B1-specific antibodies. In another embodiment, the ephrin B1-specific antibodies bind to one or more epitopes in the extracellular domain of ephrin B1. In one embodiment, the method comprises administering to the subject an amount effective of an inhibitor of tumor exosomal release. In a further embodiment, the inhibitor of tumor exosomal release comprises an inhibitor of Rab27a and/or an inhibitor of Rab27b. In another embodiment, the inhibitor of Rab27a and/or the inhibitor of Rab27b are selected from the group consisting Rab27a and/or Rab27b-specific antibodies, aptamers, small interfering RNAs, small internally segmented interfering RNAs, short hairpin RNAs, microRNAs, and/or antisense oligonucleotides. In a still further embodiment, the method further comprises administering to the subject an inhibitor of the interaction between E6 and PTPN13, or a pharmaceutically acceptable salt thereof. In one embodiment, the method further comprises administering to the subject an inhibitor of ephrin B1 phosphorylation, or a pharmaceutically acceptable salt thereof. In various further embodiments, the tumor may be an innervated solid tumor; the tumor may be selected from the group consisting of head, neck, breast, lung, liver, ovarian, colon, colorectal, brain, melanoma, pancreatic, bone, or prostate tumors; the tumor may be a high-risk human papillomavirus (HPV)-positive tumor; the HPV-positive tumor may be a tumor of the head or neck; the human papillomavirus-positive tumor of the head or neck may comprise a squamous cell carcinoma; and/or the administering may comprise local delivery to the tumor. In one embodiment, the tumor to be treated has a low level of PTPN13 expression, protein level, or protein activity level compared to control.

In another aspect is provided a method for identifying compounds to treat a tumor, comprising:
(a) contacting a first population of tumor cells with one or more test compounds; and
(b) comparing activity of exosomes released from the first population of tumor cells in promoting neurite outgrowth to activity of exosomes released from a control population of tumor cells in promoting neurite outgrowth:
wherein test compounds that reduce exosomal-promoted neurite outgrowth compared to the control are candidate compounds for treating a tumor.

In another aspect is provided a method for identifying compounds to treat a tumor, comprising:
(a) contacting a first population of tumor cells with one or more test compounds; and
(b) comparing exosomal release from the first population of cells to exosomal release from a control population of tumor cells,
wherein test compounds that reduce exosomal release compared to the control are candidate compounds for treating a tumor.

In various embodiments of either of these aspect, the first population of tumor cells and the control population of tumor cells may constitutively expresses ephrin B1, and/or the first population of tumor cells and the control population of tumor cells may be infected with human papillomavirus (HPV).

In a further aspect is provided a composition comprising:
(a) an ephrin B1 inhibitor, or a pharmaceutically acceptable salt thereof; and
(b) an inhibitor of Rab27a and/or an inhibitor of Rab27b, or a pharmaceutically acceptable salt thereof.

In one embodiment, the ephrin B1 inhibitor is selected from the group consisting ephrin B1-specific antibodies, aptamers, small interfering RNAs, small internally segmented interfering RNAs, short hairpin RNAs, microRNAs, and/or antisense oligonucleotides. In a specific embodiment, the ephrin B1 inhibitor comprises ephrin B1-specific antibodies. In another embodiment, the ephrin B1-specific antibodies bind to one or more epitopes in the extracellular domain of ephrin B1. In a further embodiment, the inhibitor of Rab27a and/or the inhibitor of Rab27b are selected from the group consisting Rab27a and/or Rab27b-specific antibodies, aptamers, small interfering RNAs, small internally segmented interfering RNAs, short hairpin RNAs, microRNAs, and/or antisense oligonucleotides. In another embodiment, the composition may further comprise an inhibitor of the interaction between E6 and PTPN13, or a pharmaceutically acceptable salt thereof. In one embodiment, the inhibitor of the interaction between E6 and PTPN13 comprises a peptide that competes with E6 for binding to PTPN13 or that competes with PTPN13 for binding to E6. In a further embodiment, the composition may further comprise an inhibitor of ephrin B1 phosphorylation, or a pharmaceutically acceptable salt thereof. In one embodiment, the inhibitor of ephrin B1 phosphorylation may comprise dasatanib, or a pharmaceutically acceptable salt thereof.

DETAILED DESCRIPTION

Figure 1:
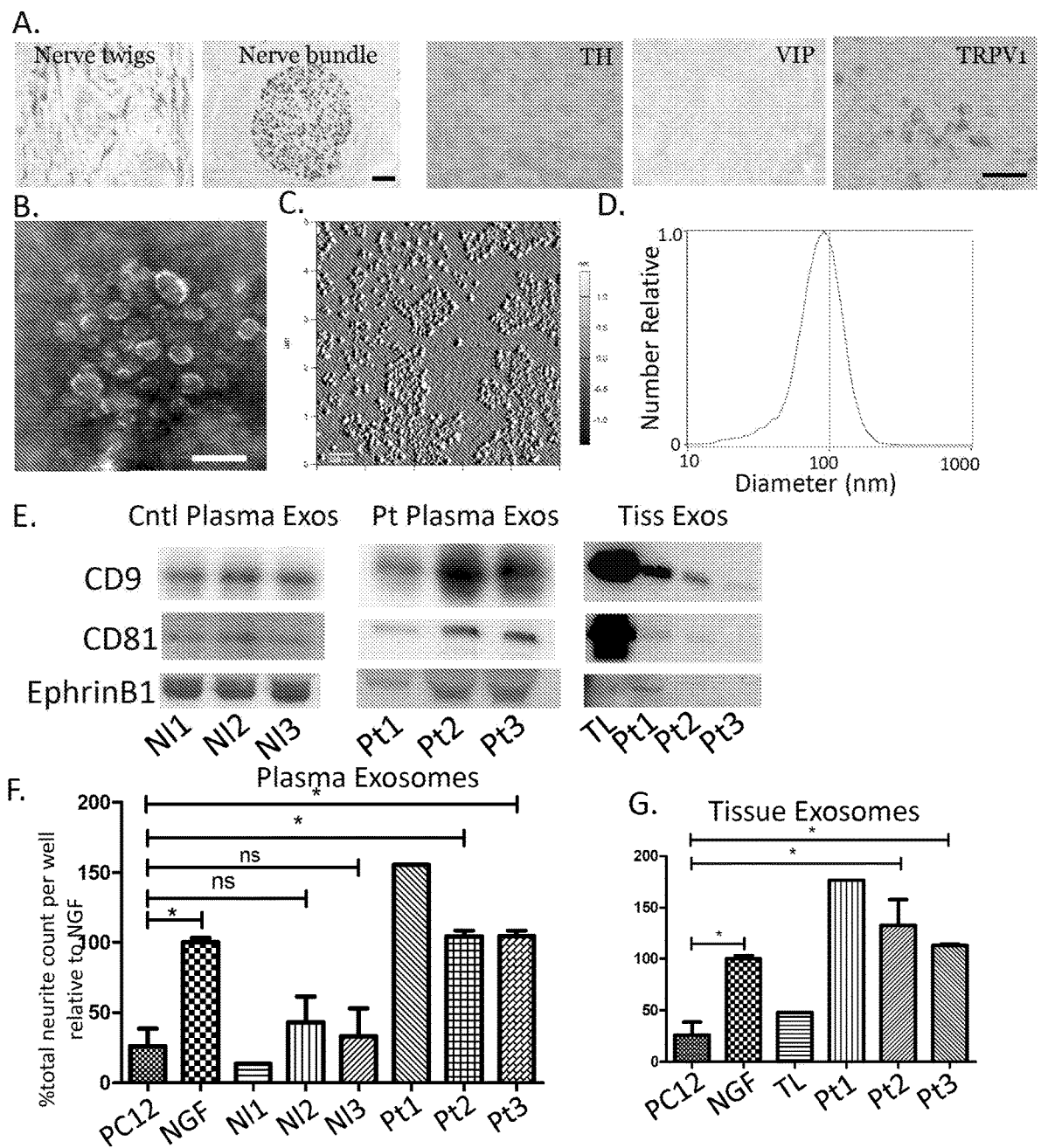
FIG. 1. Patient data. A) HNSCC: nerve "twigs" and "bundle" IHC for β-III tubulin (scale bar, 50 μm), Tyrosine Hydroxylase (TH), Vasoactive Intestinal Polypeptide (VIP) and Transient Receptor Potential Vanilloid-type one (TRPV1)(scale bar, 20 μm). Exosome scanning electron micrograph (scale bar, 200 nm) (B), atomic force microscopy amplitude trace (scale bar, 500 nm) (C) and nanoparticle tracking analysis (D). E) Control (Cntl), patient (Pt) plasma and tissue (Tiss) exosomes (Exos) western blots. Neurite outgrowth following plasma (F) or tissue (G) exosome stimulation. Nl1, Nl2, Nl3 controls; Pt1, Pt2, Pt3, patients; TL, tonsil. Student's t-test. *, $p<0.05$; **, $p<0.001$. Error bars, standard deviation.

As used herein and unless otherwise indicated, the terms "a" and "an" are taken to mean "one", "at least one" or "one or more". Unless otherwise required by context, singular terms used herein shall include pluralities and plural terms shall include the singular.

All scientific and technical terms used in this application have meanings commonly used in the art unless otherwise specified.

As used herein, "about" means+/−5% of the recited dimension or unit.

All embodiments of any aspect of the disclosure can be used in combination, unless the context clearly dictates otherwise.

In a first aspect, the disclosure provides methods for tumor treatment comprising administering to a subject having a tumor with an amount effective to limit tumor growth or metastasis of:

(a) an ephrin B1 inhibitor; and/or
(b) an inhibitor of tumor exosomal release.

As shown in the examples, that follow, the inventors have discovered that tumor derived exosomes drive neo-innervation of tumors and, moreover, that ephrin B1 within exosomes, directly or indirectly, modulates this activity. Thus ephrin B1, and/or other inhibitors of tumor exosomal release are useful to limit tumor growth or metastasis.

As used here, the terms "treating tumor growth" means (i) limiting tumor size, (ii) limiting the rate of increase in tumor size, (iii) reducing tumor innervation, (iv) limiting the rate of increase in tumor innervation, (v) limiting tumor metastases, (vi) limiting the rate of increase in tumor metastases, (vii) limiting side effects caused by tumors (i.e., pain, sickness behavior, etc.), and/or (viii) limiting the rate of increase of side effects caused by tumors.

The amount effective of the inhibitor to be administered is any amount that will achieve the goal of treating the tumor, and can be determined by one of skill in the art (such as an attending physician) in light of all circumstances, including but not limited to the type of tumor, the subject's condition, other therapeutic treatments that the subject is undergoing (i.e.: chemotherapy, radiation therapy, surgery to remove the tumor, etc.), the specific inhibitor used, and all other contributing factors.

As used herein, the term "subject" or "patient" is meant any subject for which therapy is desired, including humans, cattle, dogs, cats, guinea pigs, rabbits, rats, mice, horses, chickens, and so on. Most preferably, the subject is human.

In one embodiment, the methods serve to limit tumor innervation. As used herein, "tumor innervation" is defined as neural fibers invading in, around and/or through a tumor mass. As used herein, "limiting innervation" is defined to include any reduction (i.e., 1%, 2%, 5%, 10%, 15%, 20%, 25%, 30%, 35%, 40%, 50%, or greater reduction) in neo-innervation or existing innervation, compared to no treatment with the inhibitor.

In one embodiment, the method comprises administering an inhibitor of ephrin B1. Any suitable inhibitor of ephrin B1 may be used. In various non-limiting embodiments, the ephrin B1 inhibitor may include, but is not limited to, ephrin B1-specific antibodies, aptamers, small interfering RNAs, small internally segmented interfering RNAs, short hairpin RNAs, microRNAs, antisense oligonucleotides, or small molecule inhibitors of ephrin B1. In a specific embodiment, the inhibitor comprises ephrin B1-specific antibodies. In one non-limiting embodiment, the ephrin B1-specific antibodies bind to one or more epitopes in the extracellular domain of ephrin B1. In other embodiments, the ephrin B1-specific antibodies may bind to the PDZ binding domain and/or cytoplasmic tyrosines (i.e., those not present in the extracellular domain).

In one embodiment, the ephrin B1-specific antibodies bind to an ephrin B1 protein having the sequence shown as SEQ ID NO:1 or SEQ ID NO:2 below.

Mouse Ephrin B1 Amino Acid Sequence

Extracellular domain bold/underlined; cytoplasmic domain italicized; transmembrane domain in enlarged/outline font (SEQ ID NO: 1)
MARPGQRWLSKWLVAMVVLTLCRLATPLAKNLEPVSWSSLNPKFLSGKGL

VIYPKIGDKLDIICPRAEAGRPYEYYKLYLVRPEQAAACSTVLDPNVLVT

CNKPHQEIRFTIKFQEFSPNYMGLEFKKYHDYYITSTSNGSLEGLENREG

GVCRTRTMKIVMKVGQDPNAVTPEQLTTSRPSKESDNTVKTATQAPGRGS

QGDSDGKHETVNQEEKSGPGAGGGGSGDSDSFENSK

VALFAAVGAGCVIFLLIIIFL_TVLLLKLRKRHRKHTQQRAAAL_

_SLSTLASPKGGSGTAGTEPSDIIIPLRTTENNYCPHYEKVSGDYGHPVY_

_IVQEMPPQSPANI__YYKV_

(The last 4 amino acid residues are the PDZ binding domain)
Human Ephrin B1 Amino Acid Sequence Extracellular domain bold/underlined; cytoplasmic domain italicized; transmembrane domain in enlarged/outline font (SEQ ID NO: 2)
MARPGQRWLGKWLVAMVVWALCRLATPLAKNLEPVSWSSLNPKFLSGKGL

VIYPKIGDKLDIICPRAERPYEYYKLYLVRPEQAAACSTVLDPNVLVTCN

RPEQEIRFTIKFQEFSPNYMGLEFKKHHDYYITSTSNGSLEGLENREGGV

CRTRTMKIIMKVGQDPNAVTPEQLTTSRPSKEADNTVKMATQAPGSRGSL

GDSDGKHETVNQEEKSGPGASGGSSGDPDGFFNSK

VALFAAVGAGCVIFLLIIIFL_TVLLLKLRKRHRKHTQQRAAAL_

_SLSTLASPKGGSGTAGTEPSDIIIIPLRTTENNYCPHYEKVSGDYGH_

_PVYIVQEM PPQSPANI__YYKV_

(The last 4 amino acid residues are the PDZ binding domain)

In another embodiment, the ephrin B1-specific antibodies bind to one or more epitopes in the extracellular domain (ECD) of an ephrin B1protein, where the ECD sequence comprises or consists of the sequence shown as SEQ ID NO:3 or SEQ ID NO:4 below:

(SEQ ID NO: 3; mouse ephrin B1 extracellular domain)
MARPGQRWLSKWLVAMVVLTLCRLATPLAKNLEPVSWSSLNPKFLSGKGLVIYPKI

GDKLDIICPRAEAGRPYEYYKLYLVRPEQAAACSTVLDPNVLVTCNKPHQEIRFTIKF

QEFSPNYMGLEFKKYHDYYITSTSNGSLEGLENREGGVCRTRTMKIVMKVGQDPNA

VTPEQLTTSRPSKESDNTVKTATQAPGRGSQGDSDGKHETVNQEEKSGPGAGGGGS

GDSDSFFNSK;

(SEQ ID NO: 4; human ephrin B1 extracellular domain)
MARPGQRWLGKWLVAMVVWALCRLATPLAKNLEPVSWSSLNPKFLSGKGLVIYPK

IGDKLDIICPRAERPYEYYKLYLVRPEQAAACSTVLDPNVLVTCNRPEQEIRFTIKFQE

FSPNYMGLEFKKHHDYYITSTSNGSLEGLENREGGVCRTRTMKIIMKVGQDPNAVTP

EQLTTSRPSKEADNTVKMATQAPGSRGSLGDSDGKHETVNQEEKSGPGASGGSSGD

PDGFFNSK.

In another embodiment the ephrin B1-specific antibodies bind to an ephrin B1 protein having the amino acid sequence of SEQ ID NO:2 but which have one or more of the following amino acid changes relative to the amino acid sequence of SEQ ID NO:2:
Position 27 P to R
Position 54 P to L
Position 62 I to T
Position 98 L to S
Position 111 T to I
Position 115 Q to P
Position 119 P to T Position 119 P to S
Position 137 T to A
Position 138 S to F
Position 151 G to S
Position 151 G to V
Position 153 C to S
Position 153 C to Y
Position 155 T to P
Position 158 M to I
Position 158 M to V
Position 182 S to R These positional changes are present in variants of the human EphrinB1 protein (SEQ ID NO:2), such as variants associated with craniofrontonasal syndrome.

In another embodiment, the methods of the disclosure comprise administering to the subject an amount effective of an inhibitor of tumor exosomal release. The inhibitor of tumor exosomal release may be used alone or in combination with the ephrin B1 inhibitor. Any suitable inhibitor of tumor exosomal release may be used, including but not limited to inhibitors of Rab27a and/or Rab27b. Rab27a and Rab27b are members of the small GTPase Rab family that functions in the release of exosomes. In this embodiment, the inhibitor of Rab27a and/or the inhibitor of Rab27b include, but are not limited to Rab27a and/or the Rab27b-specific antibodies, aptamers, small interfering RNAs, small internally segmented interfering RNAs, short hairpin RNAs, microRNAs, antisense oligonucleotides, and/or small molecule inhibitors. The amino acid sequence of human and mouse Rab27a and Rab27b are provided below.

```
Human Rab27a:
                                           (SEQ ID NO: 5)
MSDGDYDYLIKFLALGDSGVGKTSVLYQYTDGKFNSKFITTVGIDFREKR

VVYRASGPDGATGRGQRIHLQLWDTAGQERFRSLTTAFFRDAMGFLLLFD

LTNEQSFLNVRNWISQLQMHAYCENPDIVLCGNKSDLEDQRVVKIEEEAI

ALAEKYGIPYFETSAANGTNISQAIEMLLDLIMKRMERCVDKSWIPEGVV

RSNGHASTDQLSEEKEKGACGC

Mouse Rab27a:
                                           (SEQ ID NO: 6)
MSDGDYDYLIKFLALGDSGVGKTSVLYQYTDGKFNSKFITTVGIDFREKR

VVYRANGPDGAVGRGQRIHLQLWDTAGQERFRSLTTAFFRDAMGFLLLFD

LTNEQSFLNVRNWISQLQMHAYCENPDIVLCGNKSDLEDQRAVKEEEARE

LAEKYGIPYFETSAANGTNISHAIEMLLDLIMKRMERCVDKSWIPEGVVR

SNGHTSADQLSEEKEKGLCGC

Human Rab27b:
                                           (SEQ ID NO: 7)
MTDGDYDYLIKLLALGDSGVGKTTFLYRYTDNKFNPKFITTVGIDFREKR

VVYNAQGPNGSSGKAFKVHLQLWDTAGQERFRSLTTAFFRDAMGFLLMFD

LTSQQSFLNVRNWMSQLQANAYCENPDIVLIGNKADLPDQREVNERQARE

LADKYGIPYFETSAATGQNVEKAVETLLDLIMKRMEQCVEKTQIPDTVNG

GNSGNLDGEKPPEKKCIC

Mouse Rab27b:
                                           (SEQ ID NO: 8)
MTDGDYDYLIKLLALGDSGVGKTTFLYRYTDNKFNPKFITTVGIDFREKR

VVYDTQGADGASGKAFKVHLQLWDTAGQERFRSLTTAFFRDAMGFLLMFD

LTSQQSFLNVRNWMSQLQANAYCENPDIVLIGNKADLPDQREVNERQARE

LAEKYGIPYFETSAATGQNVEKSVETLLDLIMKRMEKCVEKTQVPDTVNG

GNSGKLDGEKPAEKKCAC
```

The methods of the disclosure may be used to treat any suitable tumor type. In one embodiment, the tumor may be any innervated solid tumor. In various non-limiting embodiments, the methods may be used to treat head, neck, breast, lung, liver, ovaries, colon, colorectal, melanoma, brain or prostate tumors. In a further embodiment, the tumor may be a human papillomavirus (HPV)-positive tumor, including but not limited to HPV+ tumors of the head or neck. In a further non-limiting embodiment, the HPV+ tumor of the head or neck comprises a squamous cell carcinoma. In another embodiment, the tumor is positive for a high risk HPV, such as HPV16, 18, 16, 18, 31, 33, 35, 39, 45, 51, 52, 56, 58, 59 or 68. High risk HPV subtypes all have E6 proteins that contain a C-terminal PDZ binding motif (PDZBM), which binds with PDZ domain-containing proteins, such as protein-tyrosine phosphatase non-receptor type 13 (PTPN13). The HPV16 E6 oncoprotein interacts with the cellular phosphatase and tumor suppressor, PTPN13; this interaction results in degradation of PTPN13. PTPN13 interacts with ephrin B1 which is also a phosphatase substrate. Ephrin B1 is a single pass transmembrane protein ligand that binds and activates cognate Eph receptor tyrosine kinases. In addition, ephrin B1 itself becomes phosphorylated and initiates its own downstream signaling events. In HPV-infected cells, PTPN13 expression is compromised and thus ephrin B1 phosphorylation persists and contributes to an aggressive phenotype and disease progression. Thus, in a further embodiment, the methods further comprise administering to the subject an inhibitor of the interaction between E6 and PTPN13 (E6 binds to PTPN13 at PDZBM #4 of PTPN13). Any suitable inhibitor may be used, including but not limited to peptides that compete with E6 for binding to PTPN13, or that compete with PTPN13 for binding to E6. In another embodiment, the methods may further comprise administering to the subject an inhibitor of ephrin B1 phosphorylation. Any suitable inhibitor may be used, including but not limited to Src kinase inhibitors, including but not limited to dasatinib (chemical structure shown below), or a pharmaceutically acceptable salt thereof.

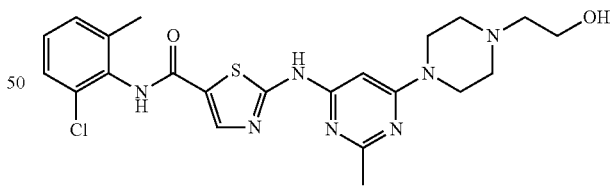

In another embodiment, the tumor has low PTPN13 expression levels or protein/protein activity levels, such as tumors in which PTPN13 expression levels or protein levels/activity are low due to promoter methylation, mRNA degradation, etc. In this embodiment, tumors with PTPN13 expression or protein level/activity below a threshold level (such as a control of normal levels of PTPN13 expression) are treated with the methods of the disclosure. In this embodiment, ephrin B1 phosphorylation would persist and the methods of the disclosure would be effective for treating such tumors. Exemplary tumor types with low to no PTPN13 expression include, but are not limited to, certain breast cancers (such as triple negative breast cancers: Révillion F, Puech C, Rabenoelina F, Chalbos D, Peyrat J P, Freiss G. Int J Cancer. 2009 Feb. 1; 124(3):638-43; Vermeer P D, Bell M, Lee K, Vermeer D W, Wieking B G, Bilal E, Bhanot G, Drapkin R I, Ganesan S, Klingelhutz A J, Hendriks W J, Lee J H. PLoS One. 2012; 7(1):e30447). See also Science. 2004 May 21; 304(5674):1164-6 in which PTPN13 may be mutated in colorectal, lung, breast, and gastric cancers, The inhibitor(s) may be administered by any suitable route, including but not limited to oral, topical, parenteral, intranasal, pulmonary, or rectal administration in dosage unit formulations containing conventional non-toxic pharmaceutically acceptable carriers, adjuvants and vehicles. In one embodiment, the inhibitor(s) is administered via local delivery, such as by direct injection into or peri-turmorally (i.e.: adjacent to the tumor and contacting the microenvironment surrounding the tumor, both of which will have exosomes that are therapy targets).

The inhibitors may be administered in association with one or more non-toxic pharmaceutically acceptable carriers and/or diluents and/or adjuvants. The inhibitor(s) may be administered as the sole therapy, or may be administered in combination with other therapeutic modalities (i.e.: chemotherapy, radiation therapy, surgical removal of the tumor, etc.).

In another aspect, the disclosure provides methods for identifying compounds to treat a tumor, comprising:

(a) contacting a first population of tumor cells with one or more test compounds; and (b) comparing activity of exosomes released from the first population of tumor cells in promoting neurite outgrowth to activity of exosomes released from a control population of tumor cells in promoting neurite outgrowth;

wherein test compounds that reduce exosomal-promoted neurite outgrowth compared to the control are candidate compounds for treating a tumor.

In a further aspect, the disclosure provides methods for identifying compounds to treat a tumor, comprising:

(a) contacting a first population of tumor cells with one or more test compounds; and (b) comparing exosomal release from the first population of cells to exosomal release from a control population of tumor cells, wherein test compounds that reduce exosomal release compared to the control are candidate compounds for treating a tumor The methods of the disclosure serve to identify compounds that reduce tumor exosomal release and/or tumor exosomal-promoted neurite outgrowth, wherein such compounds can be used to treat tumors, as discussed herein.

Measuring exosomal release and/or measuring activity of exosomes released from the first population of tumor cells in promoting neurite outgrowth can be carried out by standard methods in the art, including but not limited to the methods described in the examples that follow. The method does not require a specific amount of decrease in exosomal release and/or measuring activity of exosomes released from the first population of tumor cells in promoting neurite outgrowth compared to control, so long as the compound(s) promotes a decrease in exosomal release and/or measuring activity of exosomes released from the first population of tumor cells in promoting neurite outgrowth above that seen in the absence of test compounds.

The contacting may be carried out under any suitable conditions; those of skill in the art will be able to determine appropriate conditions in light of a specific experimental design in light of the teachings herein. The contacting can be in vitro or in vivo (ex: in an experimental animal model). In a specific embodiment, the contacting is done in vitro.

In one embodiment, the first population of tumor cells and the control population of tumor cells constitutively express ephrin B1. The tumor cells may be from any suitable tumor type. In one non-limiting embodiment, the first population of tumor cells and the control population of tumor cells are infected with human papillomavirus (HPV).

The disclosure further provides compositions comprising:

(a) an ephrin B1 inhibitor, or a pharmaceutically acceptable salt thereof; and (b) an inhibitor of Rab27a and/or an inhibitor of Rab27b, or a pharmaceutically acceptable salt thereof.

The compositions of the disclosure can be used, for example, in the methods of the invention. In various non-limiting embodiments, the ephrin B1 inhibitor may include, but is not limited to, ephrin B1-specific antibodies, aptamers, small interfering RNAs, small internally segmented interfering RNAs, short hairpin RNAs, microRNAs, antisense oligonucleotides, or small molecule inhibitors of ephrin B1. In a specific embodiment, the inhibitor comprises ephrin B1-specific antibodies. In one non-limiting embodiment, the ephrin B1-specific antibodies bind to one or more epitopes in the extracellular domain of ephrin B1. In other embodiments, the ephrin B1-specific antibodies may bind to the PDZ binding domain and/or cytoplasmic tyrosines (i.e., those not present in the extracellular domain).

In various further non-limiting embodiments, the inhibitor of Rab27a and/or the inhibitor of Rab27b include, but are not limited to Rab27a and/or the Rab27b-specific antibodies, aptamers, small interfering RNAs, small internally segmented interfering RNAs, short hairpin RNAs, microRNAs, antisense oligonucleotides, and/or small molecule inhibitors.

In a further embodiment, the compositions may further comprise an inhibitor of the interaction between E6 and PTPN13, or a pharmaceutically acceptable salt thereof. Any suitable inhibitor may be used, including but not limited to peptides that compete with E6 for binding to PTPN13, or that compete with PTPN13 for binding to E6. In another embodiment, the compositions may further comprise an inhibitor of ephrin B1 phosphorylation. Any suitable inhibitor may be used, including but not limited to Src kinase inhibitors, including but not limited to dasatanib, or a pharmaceutically acceptable salt thereof.

The composition may comprise any further components as deemed appropriate for an intended use. In various embodiments, the compositions may further comprise (a) a lyoprotectant; (b) a surfactant; (c) a bulking agent; (d) a tonicity adjusting agent; (e) a stabilizer; (f) a preservative and/or (g) a buffer. In some embodiments, the buffer in the composition is a Tris buffer, a histidine buffer, a phosphate buffer, a citrate buffer or an acetate buffer. The composition may also include a lyoprotectant, e.g. sucrose, sorbitol or trehalose. In certain embodiments, the composition includes a preservative e.g. benzalkonium chloride, benzethonium, chlorohexidine, phenol, m-cresol, benzyl alcohol, methylparaben, propylparaben, chlorobutanol, o-cresol, p-cresol, chlorocresol, phenylmercuric nitrate, thimerosal, benzoic acid, and various mixtures thereof. In other embodiments, the composition includes a bulking agent, like glycine. In yet other embodiments, the composition includes a surfactant e.g., polysorbate-20, polysorbate-40, polysorbate-60, polysorbate-65, polysorbate-80 polysorbate-85, poloxamer-188, sorbitan monolaurate, sorbitan monopalmitate, sorbitan monostearate, sorbitan monooleate, sorbitan trilaurate, sorbitan tristearate, sorbitan trioleaste, or a combination thereof. The composition may also include a tonicity adjusting agent, e.g., a compound that renders the formulation substantially isotonic or isoosmotic with human blood. Exemplary tonicity adjusting agents include sucrose, sorbitol, glycine, methionine, mannitol, dextrose, inositol, sodium chloride, arginine and arginine hydrochloride. In other embodiments, the pharmaceutical composition additionally includes a stabilizer, e.g., a molecule which, when combined with a protein of interest substantially prevents or reduces chemical and/or physical instability of the protein of interest in lyophilized or liquid form. Exemplary stabilizers include sucrose, sorbitol, glycine, inositol, sodium chloride, methionine, arginine, and arginine hydrochloride.

The compositions are typically formulated as a pharmaceutical composition, such as those disclosed above in dosage unit formulations containing conventional pharmaceutically acceptable carriers, adjuvants, and vehicles.

EXAMPLES

We utilize a murine model of human papillomavirus induced (HPV+) oropharyngeal squamous cell carcinoma (OPSCC) which consists of C57B1/6 oropharyngeal epithelial cells stably expressing HPV16 viral oncogenes, E6 and E7, H-Ras and luciferase (mEERL cells) [18-21]. The HPV16 E6 oncoprotein interacts with the cellular phosphatase and tumor suppressor, PTPN13; this interaction results in PTPN13's degradation [19, 20]. This is relevant because PTPN13 interacts with many cellular proteins including EphrinB1 which is also a phosphatase substrate. EphrinB1 is a single pass transmembrane protein ligand that binds and activates the Eph receptor tyrosine kinases. Here we show that tumor released exosomes package EphrinB1 and stimulate neurite outgrowth of PC12 cells in vitro. Compromise of EphrinB1 expression or function significantly attenuates this activity. Moreover, exosomes purified from human squamous cell carcinoma cell lines and from head and neck cancer patient plasma and tumor also package EphrinB1 as exosomal cargo and harbor neurite outgrowth activity. Consistent with these in vitro findings, mEERL tumors over-expressing EphrinB1 are significantly more innervated than tumors with compromised EphrinB1 function or expression. In addition, mEERL tumors genetically compromised in exosome release are sparsely innervated in vivo and grow slower than controls. Taken together, these data indicate that tumor released exosomes contribute to neo-neurogenesis and that exosomal EphrinB1 potentiates this activity.

Results:

Patient Exosomes Induce Neurite Outgrowth.

We tested whether patient HNSCCs are innervated by immunohistochemically (IHC) staining formalin-fixed paraffin embedded tumor tissue for β-III tubulin, a neuron specific tubulin isoform. β-III tubulin positive fibers are found coursing throughout the tissue indicating these tumors are indeed innervated (FIG. 1A, "Nerve twigs"). These β-III tubulin positive nerve "twigs" cannot be confused with perineural invasion (PNI). PNI refers to tumor invading into nerves along the perineural space; neo-neurogenesis refers to nerves invading into tumor. Within the perineural sheath, β-III tubulin positive fibers are packed tightly together in a very organized manner (FIG. 1A, "nerve bundle"). The β-III tubulin positive nerve fibers we have identified are instead coursing as individual, unorganized twigs lacking a perineural sheath (FIG. 1A "nerve twigs"). Additional IHC staining shows that HNSCCs are negative for tyrosine hydroxylase (sympathetic marker) and VIP (parasympathetic marker) but positive for TRPV1 (sensory marker) (FIG. 1A) indicating sensory neo-innervation of tumor.

Prior to testing the contribution of exosomes to neo-neurogenesis, we performed validations of our differential ultracentrifugation exosome purification technique. For human blood samples, exosomes were purified from plasma. For human tissue samples, exosomes were similarly purified from conditioned media collected after 48 hours in culture. Scanning electron microscopic analysis of our exosome preparations purified from normal donor plasma yielded vesicles consistent in shape and size (30-150 nm) with exosomes (FIG. 1B). Additionally, atomic force microscopy confirmed a 65-110 nm size (FIG. 1C) and nanoparticle tracking analysis for counting and sizing exosomes also indicated a size distribution consistent with exosomes (FIG. 1D). Taken together, these data indicate that our purification method yields vesicles consistent in size and shape with exosomes.

To test our hypothesis that tumor released exosomes induce neo-neurogenesis, we utilized PC12 cells, a rat pheochromocytoma cell line, as an in vitro screen. When stimulated with NGF (100 ng/ml), PC12 cells differentiate into neuron-like cells and extend neurites. We collected 10 ml of blood along with matched tumor tissue from three head and neck cancer patients (patient samples Pt1, Pt2, Pt3). We similarly collected blood from 3 healthy volunteers (Nl1, Nl2, Nl3) as well as adult tonsil tissue (TL). The tonsil was chosen as control tissue since the majority of HPV+ OPSCCs arise in the tonsil. Exosomes were purified, quantified by BCA protein assay and further validated by western blot analysis for the exosome markers CD9 and CD81 (FIG. 1E). To test whether they harbor neurite outgrowth activity, PC12 cells were treated with 3 μg exosomes, fixed 48 hours later and immunostained for β-III tubulin. Neurite outgrowth was quantified using the CellInSight™ CX7 High Content Analysis Platform and the number of neurites compared. The exosome yield from patient Pt1 was low allowing for analysis of only one replicate while quantities from Pt2 and Pt3 were sufficient for technical replicates. Consistent with the literature, we found that untreated PC12 cells extend very few β-III tubulin positive neurites while those stimulated with NGF do so robustly. Exosomes from all three patients (both plasma and tumor) stimulated significant neurite outgrowth of PC12 cells while exosomes from normal plasma and tonsil had minimal neurite outgrowth activity (FIG. 1 F, G). These data indicate that exosomes from head and neck cancer patients harbor neurite outgrowth activity that is absent in healthy controls.

mEERL Exosomes Induce Neurite Outgrowth.

Figure 2:
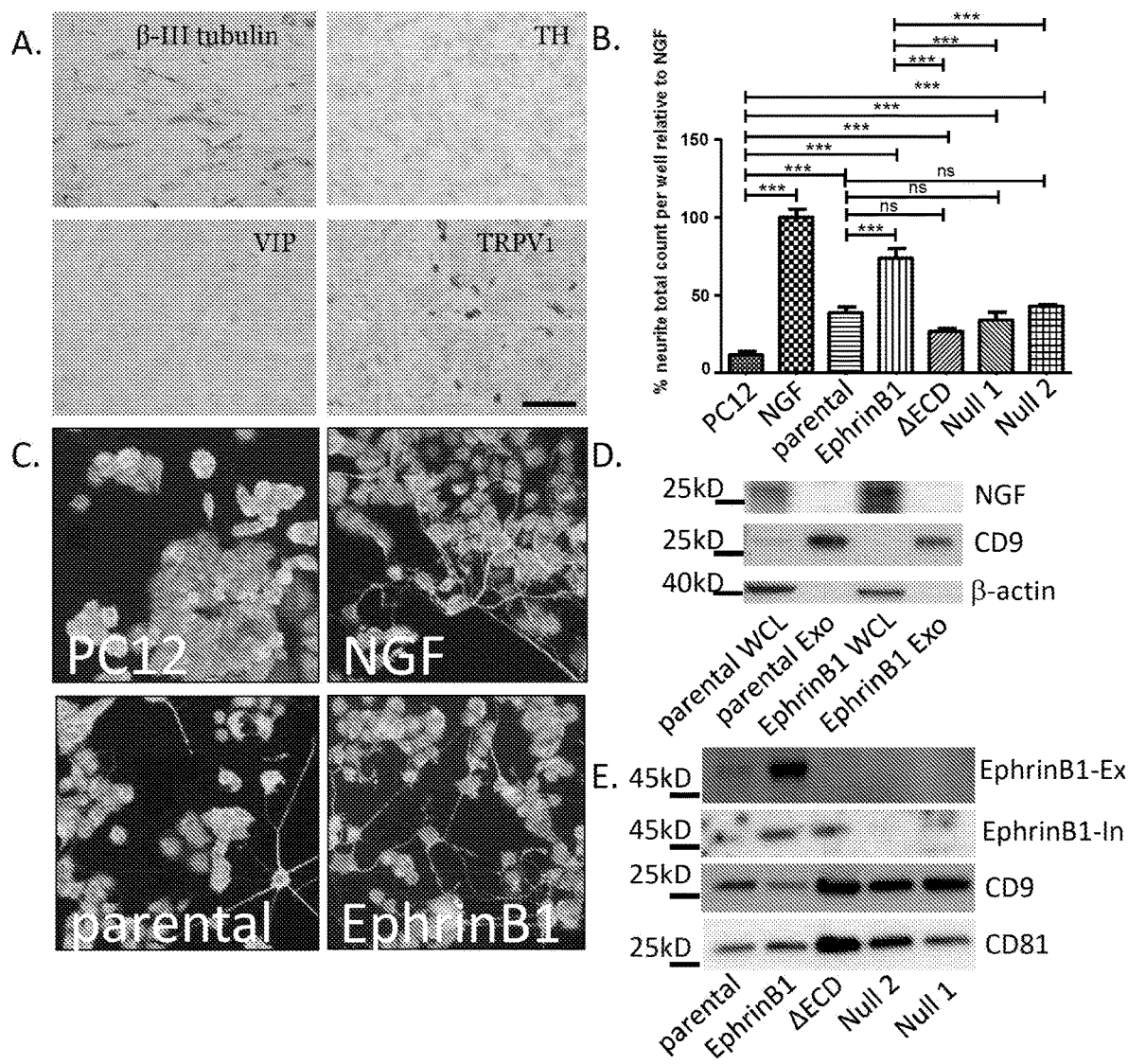
FIG. 2. mEERL exosomes and neurite outgrowth. A) IHC of mEERL tumor. Tyrosine Hydroxylase (TH), Vasoactive Intestinal Polypeptide (VIP) and Transient Receptor Potential Vanilloid-type one (TRPV1). Scale bar, 20 μm. B) Neurite outgrowth quantification following exosome treatment. Statistical analysis: one-way ANOVA, post hoc analysis by Tukey test. ***, $p<0.05$; ns, not significant. N=4 replicates/condition; experiment repeated twice. C) β-III tubulin positive immunofluorescent PC12 cells (also nuclear stained with DaPi) following exosome stimulation. D). Western blot analysis. Whole cell lysate (WCL); Exosomes (Exo). E) Western blot analysis of exosomes. EphrinB1-Ex, EphrinB1 extracellular epitope antibody. EphrinB1-In, EphrinB1 intracellular epitope antibody. Error bars, standard deviation.

To model the process of neo-neurogenesis, mice were injected with mEERL cells into the hindlimb; tumors were later harvested at endpoint, fixed, embedded and IHC stained for β-III tubulin, TH, VIP and TRPV1. Similar to patient HNSCCs, mEERL tumors harbored β-III tubulin positive nerve twigs that were sensory in nature (TRPV1 positive) (FIG. 2A). To test whether mEERL released exosomes contribute to neo-neurogenesis, cells were cultured in vitro, exosomes purified from conditioned media and tested on PC12 cells. To test the function of EphrinB1 in this process, we generated EphrinB1 modified mEERL cell lines. Stable over-expression of wild-type EphrinB1 is referred to as mEERL EphrinB1. Utilizing CRISPR/Cas9, we genetically engineered mEERL cell lines compromised in EphrinB1 function or expression. EphrinB1 deleted cells are denoted as mEERL EphrinB1 Null1 or Null2 while extracellularly deleted EphrinB1 cells are denoted as mEERL EphrinB1ΔECD. Exosomes from mEERL parental cells significantly induced neurite outgrowth of PC12 cells. Overexpression of EphrinB1 increased this activity. Interestingly, exosomes from mEERL EphrinB1ΔECD, Null 1 and Null 2 cells retain the ability to induce neurite outgrowth (FIG. 2B). Taken together, these data indicate that mEERL released exosomes promote neurite outgrowth and that while EphrinB1 is not required for this activity, it significantly potentiates it.

Exosomes Induce Neurite Outgrowth without NGF.

As mEERL cells can produce NGF, we analyzed whole cell lysates and purified exosomes from mEERL parental and EphrinB1 cells by western blot for NGF. We confirmed that mEERL parental and EphrinB1 over-expressing cells produce NGF (present in whole cell lysate, WCL), but showed that it is not packaged within CD9+ exosomes (FIG. 2D). These data indicate that NGF is not required for exosome-mediated neurite outgrowth activity. Given that exosomes purified from mEERL EphrinB1 cells potentiate neurite outgrowth of PC12 cells, we tested whether it was packaged as exosome cargo. Western blot analysis of exosomes indicated that EphrinB1 is indeed packaged within exosomes (FIG. 2E). Moreover, while the extracellular domain of EphrinB1 is absent in mEERL EphrinB1ΔECD exosomes, the intracellular domain remains as cargo. Importantly, EphrinB1 was also found in patient exosomes (FIG. 1E). As with our human exosome validation, we similarly validated exosomes purified from mEERL cells and found them to be likewise consistent in size and shape with exosomes (data not shown).

It has been suggested that more stringent methods are critical for eliminating other vesicles and cellular debris from exosome purifications. One such method requires the addition of density gradient centrifugation. To test whether this more stringent methodology purifies exosomes with neurite outgrowth activity, conditioned media from mEERL EphrinB1 cells was collected, subjected to differential ultracentrifugation and subsequently to density gradient centrifugation. Fifteen fractions were collected and fractions 4-13 were analyzed by western blot for CD9 and CD81. Consistent with the published literature, CD9+ and CD81+ vesicles were present in fraction 8; exosomes purified by differential ultracentrifugation alone ("crude" sample) were also CD9+/CD81+ (data not shown). Next, to determine which fractions retained neurite outgrowth activity, fractions 4, 5, 8 and 13 were tested on PC12 cells. "Crude" exosomes were also tested. While fraction 8 and "crude" exosomes demonstrate neurite outgrowth activity, CD9 negative fractions 4, 5 and 13 lacked this activity (data not shown). These data indicate that inclusion of density gradient centrifugation concentrates CD9+/CD81+ exosomes to a single fraction which retains neurite outgrowth activity. The data also indicate that neurite outgrowth activity is retained in EphrinB1 positive CD9+/CD81+ exosomes.

High-Risk HPV E6 and Neurite Outgrowth.

Figure 3:
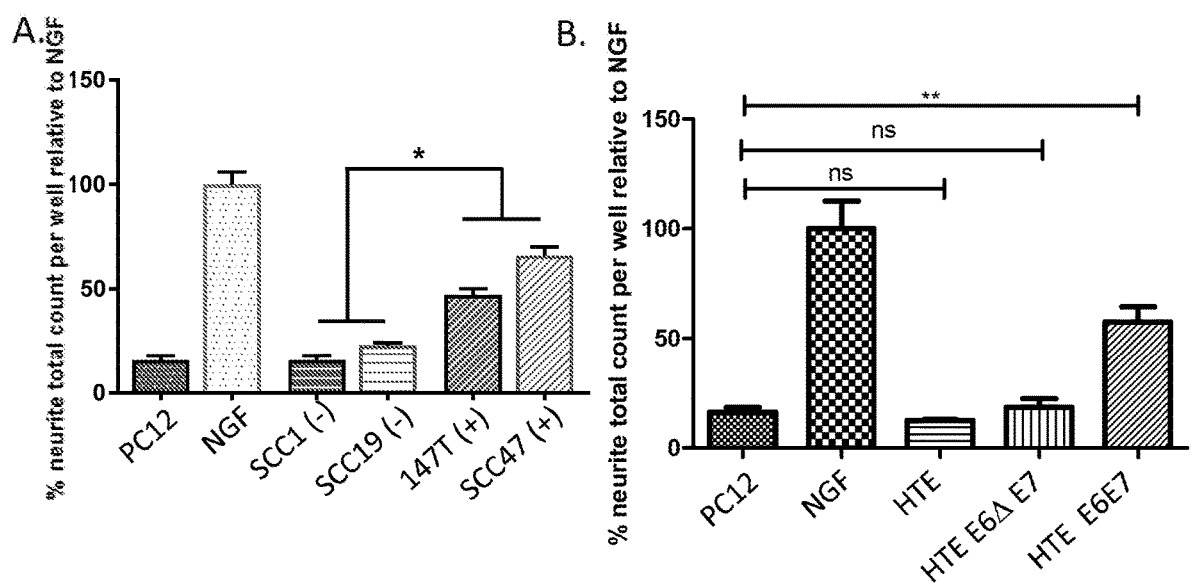
FIG. 3. HPV and neurite outgrowth. Neurite outgrowth following exosome stimulation with: A) HPV negative (−) or positive (+) human cells; statistical analysis by one-way ANOVA comparing the four lines with post hoc Tukey test for differences between HPV− and + groups. *, $p<0.001$. B) HTE, human tonsil epithelia; HTE E6ΔE7, cells expressing HPV16 E6 deleted of its PDZBM(Δ) and E7; HTE E6E7, cells expressing HPV16 E6 and E7. Statistical analysis by student's t-test. **, $p<0.05$; ns, not significant. Error bars, standard deviation. All assays: N=4 replicates/condition; experiment repeated twice.

The above studies tested neurite outgrowth activity from mEERL cells or their derivatives, all of which are HPV+. We next tested exosomes from two HPV+(SCC47 and 93-VU-147T-UP-6) and two HPV− (SCC1 and SCC19) human squamous cell carcinoma cell lines on PC12 cells and found that the HPV− exosomes harbor significantly less neurite outgrowth activity than the HPV+ exosomes (FIG. 3A). Since HPV16 induces OPSCC, it is considered a high risk HPV. Low risk HPVs rarely cause cancer. One important difference between high and low risk HPVs is found in their E6 proteins. Only high risk E6 contains a C-terminal PDZ binding motif (PDZBM) which significantly contributes to oncogenic transformation. To test the contribution of HPV16 E6 to neurite outgrowth, we tested exosomes from primary human tonsil epithelia (HTE), as well as those stably expressing HPV16 E6 and E7 (HTE E6E7) or exosomes from cells in which the PDZBM of E6 has been deleted (HTE E6ΔE7). We found that expression of full length E6 together with E7 was sufficient to induce neurite outgrowth activity while deletion of E6's PDZBM abrogated this effect (FIG. 3B). Taken together, these data suggest that HPV16 E6 contributes to neurite outgrowth activity.

Exosomes Promote Tumor Innervation and Growth.

Figure 4:
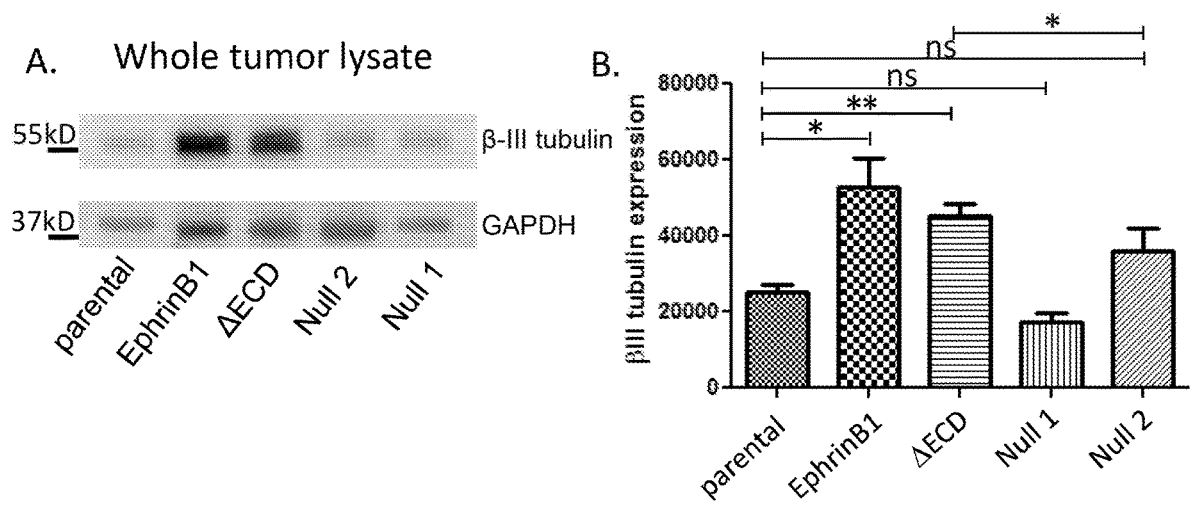
FIG. 4. Mouse tumors are innervated in vivo. A) Western blot analysis for β-III tubulin and GAPDH for the indicated tumors. B) Densitometric quantification of β-III tubulin western blots in A. β-III tubulin signal was normalized to GAPDH. N=4 tumors/condition were analyzed. Statistical analysis by student's t-test; **, $p<0.05$; *, $p<0.01$; ns, not significant. Error bars, standard deviation.

To test whether EphrinB1 expression affects tumor innervation in vivo, mice were implanted with either mEERL parental, EphrinB1, ΔECD, Null1 or Null 2 cells. Ten days post-implantation, when tumors were palpable, they were harvested and whole tumor lysate subjected to western blot analysis for β-III tubulin. β-III tubulin signals were normalized to GAPDH and quantified by densitometry. EphrinB1 and EphrinB1 ΔECD tumors harbor significantly more β-III tubulin compared to mEERL parental tumors (FIG. 4A, 4B). This in vivo capacity to induce tumor innervation was different from in vitro where EphrinB1 ΔECD exosomes induce significantly less neurite outgrowth from PC12 cells than mEERL parental exosomes (FIG. 2B). This discrepancy likely reflects components within the tumor microenvironment (absent in vitro) that also affect tumor innervation. Similar to the in vitro data, Null 1 and Null 2 tumors were not different from mEERL parental (FIGS. 2B, 4A, 4B). Taken together, these data indicate that full length and truncated EphrinB1 are sufficient to potentiate tumor innervation in vivo while its complete deletion cannot.

Figure 5:
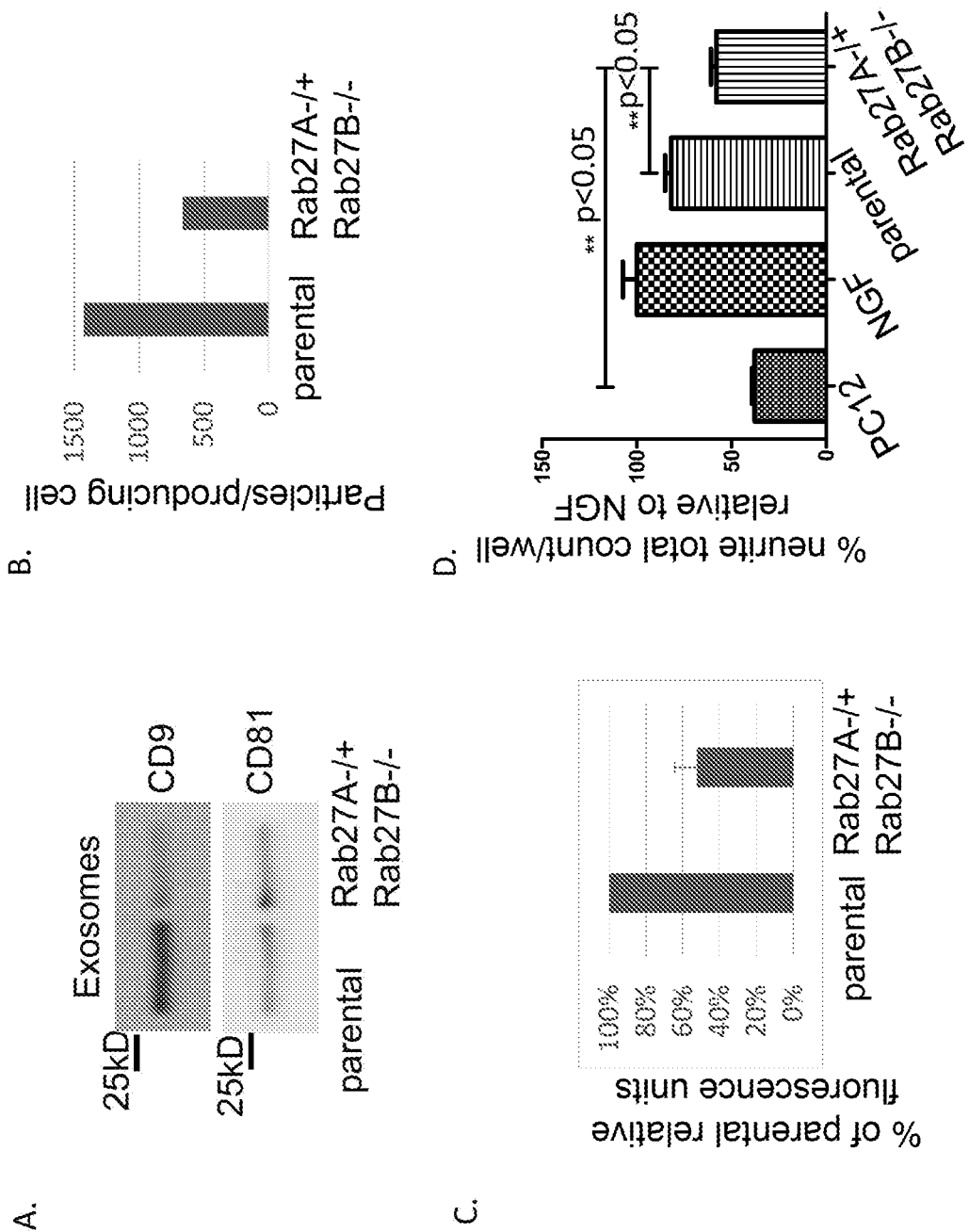
FIG. 5. Exosomes, innervation and growth. A) Western blot of exosomes; repeated N=4 with similar results. B) Particles per producing cell number; repeated N=6 with similar results. C) Relative fluorescence units of CFDA-SE labeled exosomes. N=2 samples/condition. D) Neurite outgrowth following exosome stimulation. N=4 replicates/condition; experiment repeated twice. E) Tumor growth curves; N=7 mice/condition. F) Proliferation assay. Repeated N=3 times with similar results. G) Whole tumor lysate western blot. H) Densitometric quantification of G. Exosomes normalized to producing cell number. Statistical analysis by student's t-test; ns=not significant; p values indicated; error bars, SEM.
Figure 5:
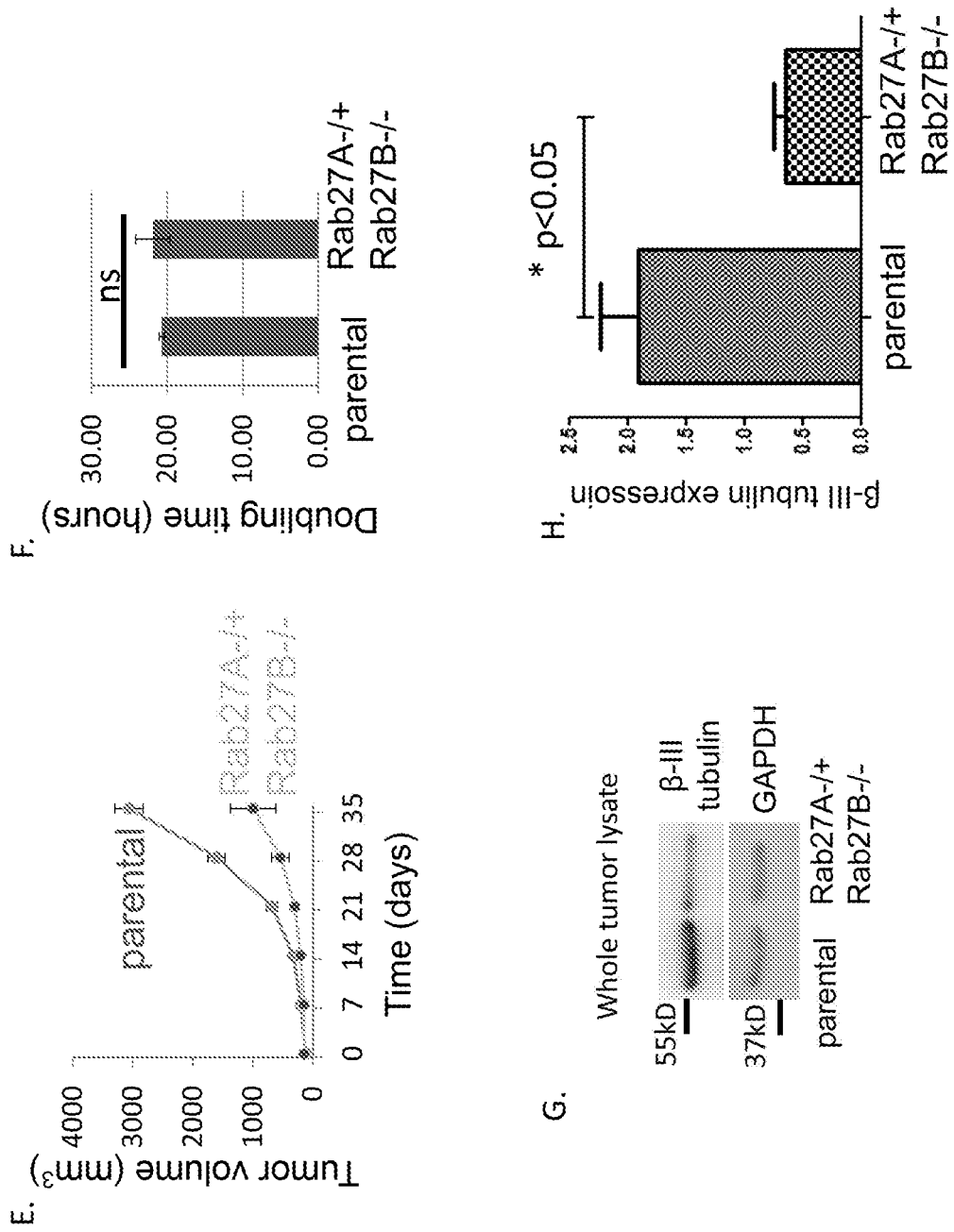

To more stringently test the hypothesis that tumor released exosomes induce tumor innervation in vivo and to define its contribution to tumor growth, we utilized CRISPR/Cas9 to genetically modify Rab27A and/or Rab27B in mEERL parental cells. These two small GTPases contribute to exosome release and their knock-down compromises release of CD9+ exosomes. The clone generated is heterozygous for Rab27A and homozygous deleted for Rab27B (mEERL Rab27A$^{-/+}$ Rab27B$^{-/-}$). Exosome samples were normalized to producing cell number. Exosomes from mEERL parental and Rab27A$^{-/+}$ Rab27B$^{-/-}$ cells were purified and analyzed for CD9 and CD81 by western blot. Exosomes purified from the Rab27A$^{-/+}$ Rab27B$^{-/-}$ expressed less CD9 which is consistent with previous studies demonstrating a decreased capacity to release exosomes by cells compromised in Rab27A/B expression which is reflected by decreased CD9 expression (FIG. 5A). Nanoparticle tracking analysis confirmed the decreased capacity of mEERL Rab27A$^{-/+}$ Rab27B$^{-/-}$ cells to release exosomes (FIG. 5B). Moreover, we labeled exosomes with CFDA-SE, a cell permeant fluorescein tracer, and quantified fluorescence. Exosomes from mEERL Rab27A$^{-/+}$ Rab27B cells had decreased fluorescence relative to mEERL parental exosomes (FIG. 5C). As a whole, these data confirm that modulation of Rab27A/B expression resulted in decreased exosome release. To test whether compromised exosome release affects neurite outgrowth of PC12 cells, mEERL parental and mEERL Rab27A$^{-/-}$ Rab27B$^{-/-}$ exosomes were normalized to producer cell number and equivalent volumes applied to PC12 cells. The neurite outgrowth activity of mEERL Rab27A$^{-/+}$ Rab27B$^{-/-}$ exosomes was significantly attenuated compared to that of exosomes from mEERL parental cells (FIG. 5D). To test whether compromised exosome release alters innervation in vivo, mice were implanted with mEERL parental or Rab27A$^{-/+}$Rab27B$^{-/-}$ cells and tumor growth monitored. Rab27A$^{-/+}$ Rab27B$^{-/-}$ tumors grew significantly slower than mEERL parental tumors in vivo (FIG. 5E). Importantly, in vitro proliferation assays show that cell doubling time was not significantly different between mEERL parental and Rab27A$^{-/+}$Rab27B$^{-/-}$ cells (FIG. 5F). To determine whether this decreased capacity to release exosomes affects tumor innervation in vivo, tumors were harvested from mice and 30 μg of whole tumor lysate quantified by western blot for β-III tubulin (FIG. 5G). Due to the delayed growth of the mEERL Rab27A$^{-/+}$Rab27B$^{-/-}$, tumors were harvested at 21 days. Consistent with our hypothesis, Rab27A$^{-/+}$ Rab27B$^{-/-}$ tumors were significantly decreased in β-III tubulin as compared to mEERL parental tumors (FIG. 5H). These data support our hypothesis that tumor released exosomes contribute to neo-neurogenesis and also suggest that neo-neurogenesis affects tumor growth.

Discussion

Our findings propose a new mechanism for tumor-induced neo-neurogenesis. We show that human and mouse HPV+HNSCCs are innervated de novo by TRPV1 positive sensory nerves. Moreover, while mEERL tumors secrete NGF, it is not required for neurite outgrowth activity in our in vitro assay nor is it packaged within exosomes. Mechanistically, packaging of full length EphrinB1 as exosome cargo significantly potentiates neurite outgrowth in vitro and tumor innervation in vivo and its deletion significantly attenuates both of these activities. Compromising release of CD9+ exosomes results in significantly decreased tumor growth and innervation in vivo. These pre-clinical studies are supported by findings with human HNSCC samples where HNSCC patient plasma and tumor exosomes harbor neurite outgrowth activity. Taken together, these data indicate that CD9+ exosomes released by HPV+ tumor cells promote tumor innervation and tumor growth in vivo. Exosomes containing EphrinB1 further potentiate this activity. HPV infection could modulate exosome cargo and, in this way, affect neurite outgrowth activity. Alternatively, the effects of HPV and EphrinB1 could be related. In HPV infected cells, E6's interaction with PTPN13 results in the degradation of this phosphatase. As a consequence, EphrinB1 phosphorylation persists. Phosphorylated EphrinB1 interacts with binding partners which could then shuttle along with it into exosomes, a theory supported by our EphrinB1ΔECD data. If HPV's contribution to neo-neurogenesis and disease progression is via this mechanism, it stands to reason that head and neck cancers would harbor either mutations in PTPN13 or EphrinB1 but not both. In fact, The Cancer Genome Atlas shows that PTPN13 and EphrinB1 alterations are mutually exclusive in HNSCC. This mutual exclusivity extends to breast, ovarian, prostate, liver, lung cancers. Thus, our findings are significant for other cancers.

It is possible that tumors induce their own innervation to provide a rich blood supply and promote tumor growth. Our data support this hypothesis. Alternatively, tumor innervation may regulate the local immune response. Neuro-immune interactions are evolutionarily conserved and critical for homeostasis. Recent clinical trials using electrical stimulation of the vagus nerve demonstrate attenuation of disease severity in rheumatoid arthritis, an autoimmune disease. These and other data support the concept that alterations in neuroimmune interactions participate in disease pathogenesis and that therapeutic modulation of these interactions can restore homeostasis. Thus, tumors may promote their own innervation as a means to dampen immune responses, promote tumor tolerance, disease progression and dissemination.

Methods:

Antibodies

Antibodies Utilized for Western Blot Analysis Included:

anti-CD9 (Abcam, 1:1,000), anti-CD81 (clone B-11, 1:1,000, Santa Cruz), anti-Ephrin B1 (ECD epitope, R&D Systems, 1:500), anti-human EphrinB1 (ICD epitope, LifeSpan BioSciences, 1:500), anti-β-III Tubulin (2G10, 1:5,000, Abcam), anti-GAPDH (Ambion, 1:5,000). HRP-coupled secondary antibodies were purchased from Thermo-Fisher.

Antibodies Utilized for IHC:

anti-β-III Tubulin (2G10, 1:250, Abcam), anti-Tyrosine Hydroxylase (Ab112, 1:750, Abcam), anti-TRPV1 (cat #ACC-030, 1:100, Alomone labs), anti-VIP (ab22736, 1:100, Abcam).

Antibody Utilized for Quantification on the CX7:

anti-β-III tubulin (Millipore, AB9354).

Cell Lines:

All cell lines have been authenticated by STR (BioSynthesis). In addition, all cell lines have been confirmed as mycoplasma free as per Uphoff and Drexler (In Vitro Cell Dev Biol Anim, 2002. 38(2): p. 79-85).

Human:

UM-SCC1 and UM-SCC47 cell lines were maintained with DMEM with 10% fetal calf serum and 1% penicillin/streptomycin.

Primary human tonsil epithelia were collected under an approved IRB protocol and maintained with KSFM (Gibco, cat #10724-011). HTE E6/E7 and HTE E6A/E7 were generated by retroviral transduction and maintained in E-media as described above.

Mouse:

mEERL cells (parental and all derivatives) were maintained with E-medium (DMEM (Corning, cat #10-017-CV)/Hams F12 (Corning, cat #10-080-CV), 10% exosome depleted fetal calf serum, 1% penicillin/streptomycin, 0.5 μg/ml hydrocortisone, 8.4 ng/ml cholera toxin, 5 μg/ml transferrin, 5 μg/ml insulin, 1.36 ng/ml tri-iodo-thyonine, and 5 ng/ml EGF.

mEERL EphrinB1 CRISPR Clones:

Two distinct strategies were utilized to generate EphrinB1 null mEERL cell lines; one strategy employed simultaneous double-targeting to remove a large portion of gDNA spanning exons 1-5 and one utilized single-targeting to produce frame-shift causing indels leading to early termination. Target selection and guide sequence cloning were carried out using the tools and protocol of Ran et al. (Nat Protoc, 2013. 8(11): p. 2281-2308). PCR assays for the double targeting strategy employed primers external to (1-5Δ Ext.) or within (1-5Δ Int.) the predicted deletion site (Table 1). The external assay should result in a 10,485 bp wt amplicon and a 229 bp Δ amplicon while the internal assay produces a 330 bp wt amplicon and no A amplicon. Single target screening utilized PCR to amplify a 330 bp region surrounding the target site followed by restriction digest with BslI, the recognition site of which should be destroyed when double strand breaks are incorrectly repaired (Table 1).

Clone mEERL EphrinB1ΔECD:

This clone was generated from the double-targeting strategy. PCR assays show the predicted deletion product using primers external to the targeted region and lack of an amplicon using primers within the deletion. The sequence data showed that Exons 2-4 are deleted; these exons comprise the majority of the extracellular domain of EphrinB1 (data not shown). The 5' end of the deletion in exon 1 occurs just after the signal peptide while the 3' end of the deletion in exon 5 is within the transmembrane (TM) domain. Eight amino acids within the TM domain are deleted, however, two additional hydrophobic alanines are incorporated.

Clones mEERL EphrinB1 Null 1 and Null 2.

mEERL EphrinB1 Null1 and Null 2 clones were generated with the single targeting strategy. Sequence data from these clones indicated a 1 bp insertion (Null 2) and 10 bp deletion (Null 1), both leading to frame shifts and early termination codons. In the CRISPR strategy employed, positive clones show a lack of cutting with the restriction enzyme, BslI. mEERL EphrinB1 Null 1 and Null 2 clones do not cut with this enzyme (data not shown).

TABLE 1

Primer sequences used to screen clones.

| Primer | Sequence |
| --- | --- |
| 1-5Δ Ext. FWD | 5'-ATCCTGAAGTGCATTCTGCC-3' (SEQ ID NO: 9) |
| 1-5Δ Ext. REV | 5'-TAGGGTACTGAGCGAGAGG-3' (SEQ ID NO: 10) |
| 1-5Δ Int. FWD | 5'-TGGCCTTCACTGTCATAGC-3' (SEQ ID NO: 11) |
| 1-5Δ Int. REV | 5'-TTCCAGGCCCATGTAGTTG-3' (SEQ ID NO: 12) | mEERL Rab27 CRISPR Clones:

Knockouts of Rab27 in mEERL cells were created using the general protocol of Ran et al. Briefly, guide sequences targeting exons of RAB27A, RAB27B, or both were cloned into pSpCas9(BB)-2A-Zeo and transfected singly or in combinations to produce indels or larger deletions, respectively, in one or both genes. Following 5 days of Zeocin selection, single cells were expanded and screened for loss of restriction enzyme sites due to indels or by PCR for large deletions induced by double-targeting. Using this strategy, a single clone was identified for sequencing and further characterization.

Clone mEERL Rab27A$^{-/+}$Rab27B$^{-/-}$:

Resulted from a strategy for double knock out of RAB27A and RAB27B in which sgRNA's targeted to exon 4 of RAB27A, exon 4 of RAB27B, and a sequence of exon 3 shared by RAB27A and B were co-transfected. PCR revealed a heterozygous, truncated deletion product for Rab27A and the expected homozygous deletion amplicon for Rab27B (data not shown). RAB27B sequence data indicated distinct repair products at the deletion site; although one allele exhibits an immediate stop codon, it is unclear where the other might terminate. However, western blotting confirms lack of detectable protein (data not shown).

PC12 Cells:

PC12 cells were purchased from ATCC and maintained with DMEM with 10% horse serum (Gibco, cat #26050-088) and 5% fetal calf serum. When used for neurite outgrowth assays, PC12 cells were maintained with DMEM with 1% horse serum and 0.5% fetal calf serum.

Imaging:

Electron Microscopy:

Exosome samples were processed and analyzed by the Microscopy and Cell Analysis Core at Mayo Clinic.

Atomic Force Microscopy (AFM):

Purified exosomes were diluted 1:10 in de-ionized water, added to a clean glass dish, and allowed to air-dry for 2 hours before drying under a gentle stream of nitrogen. Exosomes deposited on glass dish were characterized using an AFM (Model: MFP-3D BIO™, Asylum Research, Santa Barbara, Calif.). Images were acquired in AC mode in air using a silicon probe (AC240TS-R3, Asylum Research) with a typical resonance frequency of 70 kHz and spring constant of 2 Nm$^{-1}$. Height and amplitude images were recorded simultaneously at 512×512 pixels with a scan rate of 0.6 Hz. Image processing was done using Igor Pro 6.34 (WaveMetrics, Portland, Oreg.) and analyzed with Image J.

Immunohistochemistry. Tissues were fixed in 10% neutral buffered formalin and processed on a Leica 300 ASP tissue processor. Human (N=30) and mouse (N=20) tumor blocks were sectioned at 5 μm. The BenchMark® XT automated slide staining system (Ventana Medical Systems, Inc.) was used for the optimization and staining. The Ventana iView DAB detection kit was used as the chromogen and the slides were counterstained with hematoxylin. Omission of the primary antibody served as the negative control.

PC12 Assay and β-III Tubulin Quantification by CX7.

The CellInSight CX7 High Content Analysis Platform performs automated cellular imaging for quantitative microscopy which was utilized to quantify neurite outgrowth. 7.5×10$^4$ PC12 cells were seeded onto 96 well black optical bottom, flat bottom plates (ThermoFisher) and 48 hours after treatment were fixed with 4% paraformaldehyde and then blocked and permeabilized with a solution containing 3% donkey serum, 1% BSA, and 0.5% Triton-X 100. Staining for β-III tubulin (Millipore, AB9354) was followed by Alexa Fluor™ 488 goat anti-chicken IgG and Hoechst 33342. Washes were performed with PBS. Neurite outgrowth analysis was performed on the CellInsight™ CX7 HCS (ThermoFisher) using the Cellomics Scan Software's (Version 6.6.0, ThermoFisher) Neuronal Profiling Bioapplication (Version 4.2). Twenty-five imaging fields were collected per well with a 10× objective with 2×2 binning Nuclei were identified by Hoechst-positive staining, while cell somas and neurites were identified by β-III tubulin-positive immunolabeling. Cells were classified as neurons if they had both a Hoechst-positive nucleus as well as a β-III tubulin positive soma. Only neurites longer than 20 μm were included in the analysis. All assays utilizing exosomes from cell lines were run with an N=4 replicates per condition and repeated at least two times with similar results. Assays utilizing human samples were limited in materials and replicates were run to the extent possible as noted in the text.

Exosome Purification:

Differential Ultracentrifugation.

500,000 cells were seeded onto a 150 mm$^2$ plate and incubated in medium containing 10% fetal calf serum that was depleted of exosomes. Fetal calf serum exosome depletion consisted of an over-night ultracentrifugation at 100,000×g. Conditioned medium was collected after 48 hours and exosomes were purified by differential ultracentifugation as described by Kowal et. al. (Proc Nati Acad Sci USA, 2016. 113(8): p. E968-77) with some modifications. Briefly, conditioned medium was centrifuged at 300×g for 10 min at 4° C. to pellet cells. Supernatant was centrifuged at 2,000×g for 20 min at 4° C., transferred to new tubes, and centrifuged for 30 min at 10,000×g, and finally in a SureSpin 630/17 rotor for 120 min at 100,000×g. All pellets were washed in PBS and re-centrifuged at the same speed and re-suspended in 200 μL of sterile PBS/150 mm dishes.

Differential Ultracentrifugation and Optiprep Density Gradient.

Following differential ultracentrifugation as described above, a discontinuous iodixanol gradient was utilized. Solutions of 5, 10, 20 and 40% iodixanol were made by mixing appropriate amounts of a homogenization buffer [0.25 M sucrose, 1 mM EDTA, 10 mM Tris-HCL, (pH 7.4)]

and an iodixanol solution. This solution was prepared by combining a stock solution of OptiPrep™ (60% (w/v) aqueous iodixanol solution, Sigma) and a solution buffer [0.25 M sucrose, 6 mM EDTA, 60 mM Tris-HCl, (pH 7.4)]. The gradient was formed by layering 4 mL of 40%, 4 mL of 20%, 4 mL of 10% and 3 mL of 5% solutions on top of each other in a 15.5 mL open top polyallomer tube (Beckman Coulter). 400 µl of crude exosomes (isolated by differential ultracentrifugation) were overlaid onto the top of the gradient which was then centrifuged for 18 hours at 100,000 g and 4° C. (SureSpin 630/17 rotor, ThermoScientific™ Sorvall™) Gradient fractions of 1 mL were collected from the top of the self-forming gradient, diluted to 14 mL in PBS and centrifuged for 3 hours at 100,000 g and 4° C. The resulting pellets were re-suspended in 100 µL PBS and stored at −80° C.

Exosome Purification from Human Plasma.

Ten ml of whole blood were pipetted directly onto Ficoll-loaded Leucosep tubes and centrifuged at room temperature for 30 minutes at 800×g with the brake off. Exosomes were isolated from the recovered plasma by differential ultracentrifugation as described.

Exosome Purification from Human Tumor.

Fresh tumor tissue was cut into small pieces and placed in culture with KSFM (keratinocyte serum free medium) containing Fungizone (Thermo Fisher) and maintained in culture for 48 hours. Conditioned media was collected and exosomes harvested by differential ultracentrifugation as described.

Protein Analysis.

BCA Protein Assay of Exosomes.

The standard BCA protein assay was utilized with modifications to accommodate the low protein yield from exosome preparations. Briefly, 5 µl of 10% TX-100 (Thermo Scientific) were added to an aliquot of 50 µl of purified exosomes and incubated 10 minutes at room temperature. A working ratio of 1:11 was used and incubated in a 96 well plate for 1 hr at 37° C. Absorbance at 562 nm was then measured (SpectraMax™ Plus 384) and protein concentration estimated from a quartic model fit to the BSA standard curve.

Western Blot Analysis.

Sample protein concentration was determined by BCA protein assay as described. Equal total protein was separated by SDS-PAGE, transferred to PVDF membranes (Immobilon™-P, Millipore), blocked with either 5% Bovine Albumin Fraction V (Millipore) or 5% milk (Carnation instant non-fat dry milk), washed in TTBS (0.05% Tween-20, 1.37M NaCl, 27 mM KCl, 25 mM Tris Base), and incubated in primary antibody. Washed membranes were incubated with HRP-conjugated secondary antibody, incubated with chemiluminescent substrate (ThermoScientific, SuperSignal™ West Pico) and imaged using a UVP BioImaging System.

In Vivo Studies.

All animal studies were performed under approved institutional IACUC protocols and within institutional guidelines. All animal experiments utilized 4-8 week old male C57Bl/6 mice (The Jackson Laboratory) which were maintained at the Sanford Research Laboratory Animal Research Facility in accordance with USDA guidelines.

Mouse Tumor Experiments:

Tumors were initiated as follows: using a 23-gauge needle, mEERL cells ($1 \times 10^5$ cells) were implanted subcutaneously in the right hindlimb of mice. Tumor growth was monitored weekly by caliper measurements. Mice were euthanized when tumor volume was greater than 1.5 cm in any dimension. N=4 mice/group for quantification of β-III tubulin by western blot. N=7 mice/group for tumor growth.

Whole Tumor Lysates.

Tumors were harvested 10 or 21 days post-implantation (as per text) and homogenized in lysis buffer on ice using a tissue homogenizer (Omni TH International). The homogenate was then sonicated and centrifuged at 2000 g for 5 min. The resulting supernatant was collected and further centrifuged at 13000 g for 10 min prior to BCA protein concentration estimation. Western blots were conducted using 30 µg inputs. Beta-III tubulin western blots of whole tumor lysates from N=4 tumors/condition. Signals were quantified by densitometry using VisionWorks™ LS software and normalized to GAPDH. Group averages were compared using student's t-test.

Human Samples.

All human samples were collected under an approved Institutional Review Board protocol with signed Informed Consent. Samples included adult (age≥18 years) patients of both sexes and all races with a diagnosis of primary or locally advanced, squamous cell carcinoma of the head and neck (anatomic sites: oral cavity, oropharynx, hypopharynx, and larynx).

Statistical Analysis.

Data were analyzed and graphed using PrismGraph™. Descriptive statistics are presented as mean±SEM or standard deviation (see Figure legends). Unpaired student's t-test or one-way ANOVA were utilized for statistical analysis as indicated in the figure legends. PC12 assays utilizing exosomes from cell lines were run with four technical replicates for each condition and experiments were repeated at least 2 times. PC12 assays utilizing exosomes from human samples (blood or tumor) were treated differently as these samples were very limited. Thus, exosomes for each human sample were tested in duplicate when possible. When samples were limited (noted in text) only one well was tested.

Example 2

This example demonstrates that other solid tumors (exemplified by colorectal, melanoma and breast tumors) also release factors which may also include exosomes and that these factors contribute to tumor innervation. We harvested conditioned media from colorectal (CT26), melanoma (B16) and breast tumor (4T1) cell lines and tested on PC12 cells. CT26 is a cell line derived from a BALB/c mouse that was treated with N-nitroso-N-methylrethane. This cell line is widely used to study colorectal cancer. B16 is a melanoma mouse cancer cell line that spontaneously arose in a C57Bl/6 mouse. it is widely used to study melanoma. 4T1 is a 6-thioguanine resistant cell line selected from the 410.4 (a mouse mammary adenocarcinoma cell line) tumor without mutagen treatment. When implanted into BALB/c mice, 4T1 cells are highly metastatic and go to the lungs, liver, lymph nodes and brain. This cell line is highly used as an animal model of stage IV human breast cancer. PC12 is a rat pheochromocytoma cell line and the cells are undifferentiated unless stimulated with a growth factor such as nerve growth factor, after which they turn into neuron-like cells. The CT26, B16 and 4T1 cell lines were seeded at approximately 40% confluence and conditioned media harvested 48 hours later (when cells were approximately 90% confluent). The conditioned media was then used to treat PC cells for 24 hours. After treatment, the PC12 cells were fixed and stained for beta-III tubulin and quantified on the CX7.

Figure 6:
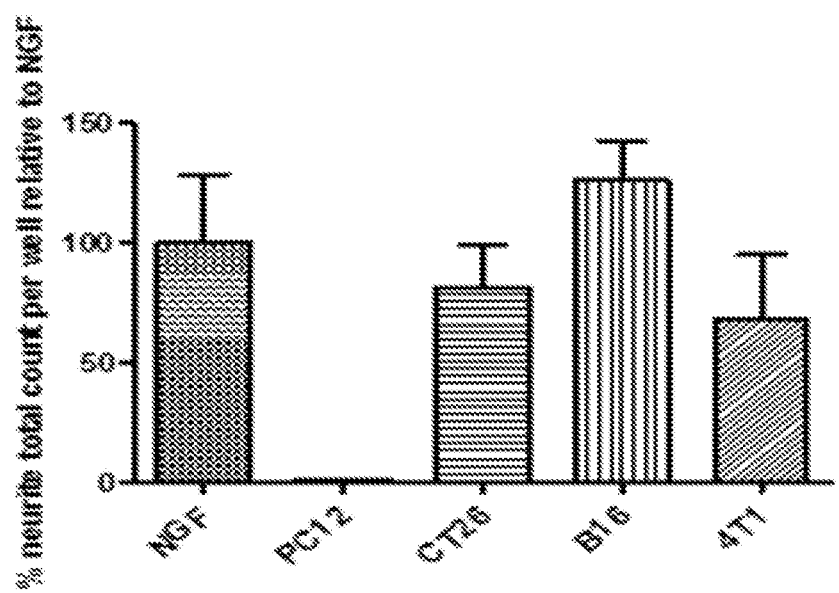
FIG. 6. PC12 cells were treated with conditioned media from CT26 (colorectal cancer cell line), B16 (melanoma cancer cell line) or 4T1 (breast cancer cell line) for 24 hours and neurite outgrowth was quantified. PC12 cells treated with recombinant NGF (NGF) served as a positive control, while untreated PC12 cells (PC12) served as the negative control.

In this assay, we put conditioned media on PC12 cells to see if there is something released by colorectal, melanoma and breast tumor cell lines that can induce neuronal differentiation of the PC12 cells. Following stimulation (24 hour) with the conditioned media from the different cell lines, PC12 cells were fixed and stained for beta-III tubulin. The extent of beta-III tubulin staining was quantified on the CX7. The total number of beta-III tubulin positive neurites per well for each condition are graphed in FIG. 6. In all such experiment, unstimulated PC12 cells (PC12) serve as the negative control as they do not extend many neurites. The positive control consists of PC12 cells stimulated with 100 ng/ml of recombinant NGF which leads to robust neurite outgrowth. Following quantification of beta-III tubulin staining, the NGF condition is set at 100% and all other conditions are relative to that.

The experiment was done using conditioned media from the different cell line. We have since purified exosomes from these cell lines and tested similarly. The results (data not shown) demonstrate that exosomes also promote neurite outgrowth though not to the level that full conditioned media can, indicating that a combination of exosomes and other released factors, such as neurotrophic factors, induce neurite outgrowth from these types of tumors.

Example 3

Figure 7:
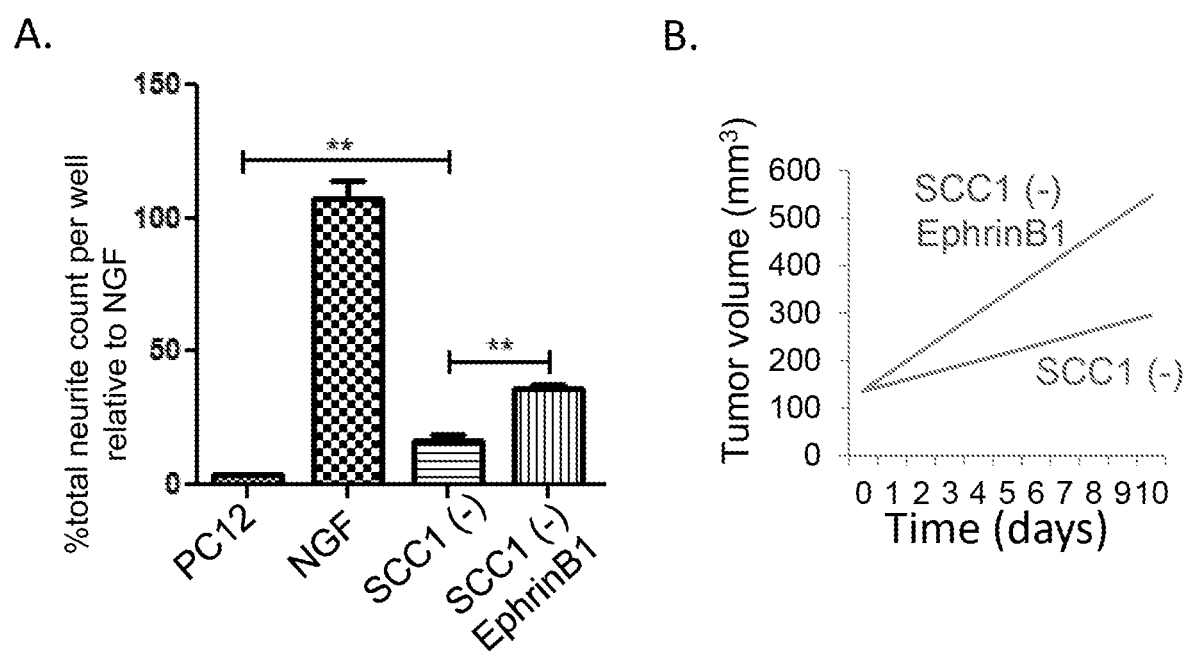
FIG. 7. (A) Graph showing effect of over-expressing EphrinB1 in an HPV negative squamous cell carcinoma cell line on neurite outgrowth. (B) Graph showing tumor growth rate in immune incompetent NOD SCID mice implanted with either SCC1 or SCC1-EphrinB1 cells.

Given the effect of E6 on PTPN13 and EphrinB1 activation, we wondered if merely over-expressing EphrinB1 in an HPV negative squamous cell carcinoma cell line, would be sufficient to promote increased neurite outgrowth. Thus, we stably over-expressed EphrinB1 in SCC1 cells and tested exosomes on PC12 cells. Exosomes from SCC1-EphrinB1 cells induced significantly more neurite outgrowth than those from the SCC1 parental cells (FIG. 7A). To determine if this increased activity similarly affected tumor innervation, immune incompetent NOD SCID mice were implanted with either SCC1 or SCC1-EphrinB1 cells (N=5 mice/group) and tumor growth monitored for 10 days. SCC1-EphrinB1 tumors grew significantly faster than SCC1 parental tumors (FIG. 7B).

I claim:

1. A method for cancerous tumor treatment comprising administering to a subject having a cancerous tumor an amount effective to limit tumor growth or metastasis of an ephrin B1 antibody or a pharmaceutically acceptable salt thereof, wherein the administering comprises direct injection into the tumor or peri-tumoral administration, and wherein the tumor is an innervated solid tumor.

2. The method of claim 1 wherein the ephrin B1 antibody binds to one or more epitopes in the extracellular domain of ephrin B1.

3. The method of claim 1, wherein the tumor is selected from the group consisting of head and neck, breast, lung, liver, ovarian, colon, colorectal, brain, melanoma, pancreatic, bone, and prostate tumors.

4. The method of claim 1, wherein the tumor is a high-risk human papillomavirus (HPV)-positive tumor.

5. The method of claim 4 wherein the HPV-positive tumor is a tumor of the head and neck.

6. The method of claim 5, wherein the human papillomavirus-positive tumor of the head and neck comprises a squamous cell carcinoma.

7. A method for limiting cancerous tumor innervation, comprising administering to a subject having a cancerous tumor an amount effective to limit tumor innervation of an ephrin B1 antibody, wherein the administering comprises direct injection into the tumor or peri-tumoral administration, and wherein the tumor is an innervated solid tumor.

8. The method of claim 7, wherein the ephrin B1 antibody binds to one or more epitopes in the extracellular domain of ephrin B1.

9. The method of claim 7, wherein the tumor is selected from the group consisting of head and neck, breast, lung, liver, ovarian, colon, colorectal, brain, melanoma, pancreatic, bone, or prostate tumors.

10. The method of claim 7, wherein the tumor is a high-risk human papillomavirus (HPV)-positive tumor.

11. The method of claim 10 wherein the HPV-positive tumor is a tumor of the head and neck.

12. The method of claim 11, wherein the human papillomavirus-positive tumor of the head and neck comprises a squamous cell carcinoma.

* * * * *

SEQUENCE LISTING

```
<160> NUMBER OF SEQ ID NOS: 12

<210> SEQ ID NO 1
<211> LENGTH: 345
<212> TYPE: PRT
<213> ORGANISM: Artificial Sequence
<220> FEATURE:
<223> OTHER INFORMATION: Synthetic

<400> SEQUENCE: 1

Met Ala Arg Pro Gly Gln Arg Trp Leu Ser Lys Trp Leu Val Ala Met
1               5                   10                  15

Val Val Leu Thr Leu Cys Arg Leu Ala Thr Pro Leu Ala Lys Asn Leu
                20                  25                  30

Glu Pro Val Ser Trp Ser Ser Leu Asn Pro Lys Phe Leu Ser Gly Lys
            35                  40                  45

Gly Leu Val Ile Tyr Pro Lys Ile Gly Asp Lys Leu Asp Ile Ile Cys
        50                  55                  60

Pro Arg Ala Glu Ala Gly Arg Pro Tyr Glu Tyr Tyr Lys Leu Tyr Leu
65                  70                  75                  80

Val Arg Pro Glu Gln Ala Ala Ala Cys Ser Thr Val Leu Asp Pro Asn
                85                  90                  95

Val Leu Val Thr Cys Asn Lys Pro His Gln Glu Ile Arg Phe Thr Ile
            100                 105                 110

Lys Phe Gln Glu Phe Ser Pro Asn Tyr Met Gly Leu Glu Phe Lys Lys
        115                 120                 125

Tyr His Asp Tyr Tyr Ile Thr Ser Thr Ser Asn Gly Ser Leu Glu Gly
    130                 135                 140

Leu Glu Asn Arg Glu Gly Gly Val Cys Arg Thr Arg Thr Met Lys Ile
145                 150                 155                 160

Val Met Lys Val Gly Gln Asp Pro Asn Ala Val Thr Pro Glu Gln Leu
                165                 170                 175

Thr Thr Ser Arg Pro Ser Lys Glu Ser Asp Asn Thr Val Lys Thr Ala
            180                 185                 190

Thr Gln Ala Pro Gly Arg Gly Ser Gln Gly Asp Ser Asp Gly Lys His
        195                 200                 205

Glu Thr Val Asn Gln Glu Glu Lys Ser Gly Pro Gly Ala Gly Gly Gly
```

```
            210                 215                 220
Gly Ser Gly Asp Ser Asp Ser Phe Phe Asn Ser Lys Val Ala Leu Phe
225                 230                 235                 240

Ala Ala Val Gly Ala Gly Cys Val Ile Phe Leu Ile Ile Ile Phe
                245                 250                 255

Leu Thr Val Leu Leu Leu Lys Leu Arg Lys Arg His Arg Lys His Thr
                260                 265                 270

Gln Gln Arg Ala Ala Ala Leu Ser Leu Ser Thr Leu Ala Ser Pro Lys
                275                 280                 285

Gly Gly Ser Gly Thr Ala Gly Thr Glu Pro Ser Asp Ile Ile Pro
290                 295                 300

Leu Arg Thr Thr Glu Asn Asn Tyr Cys Pro His Tyr Glu Lys Val Ser
305                 310                 315                 320

Gly Asp Tyr Gly His Pro Val Tyr Ile Val Gln Glu Met Pro Pro Gln
                325                 330                 335

Ser Pro Ala Asn Ile Tyr Tyr Lys Val
                340                 345

<210> SEQ ID NO 2
<211> LENGTH: 344
<212> TYPE: PRT
<213> ORGANISM: Artificial Sequence
<220> FEATURE:
<223> OTHER INFORMATION: Synthetic

<400> SEQUENCE: 2

Met Ala Arg Pro Gly Gln Arg Trp Leu Gly Lys Trp Leu Val Ala Met
1               5                   10                  15

Val Val Trp Ala Leu Cys Arg Leu Ala Thr Pro Leu Ala Lys Asn Leu
                20                  25                  30

Glu Pro Val Ser Trp Ser Ser Leu Asn Pro Lys Phe Leu Ser Gly Lys
            35                  40                  45

Gly Leu Val Ile Tyr Pro Lys Ile Gly Asp Lys Leu Asp Ile Ile Cys
    50                  55                  60

Pro Arg Ala Glu Arg Pro Tyr Glu Tyr Tyr Lys Leu Tyr Leu Val Arg
65                  70                  75                  80

Pro Glu Gln Ala Ala Ala Cys Ser Thr Val Leu Asp Pro Asn Val Leu
                85                  90                  95

Val Thr Cys Asn Arg Pro Glu Gln Glu Ile Arg Phe Thr Ile Lys Phe
                100                 105                 110

Gln Glu Phe Ser Pro Asn Tyr Met Gly Leu Glu Phe Lys Lys His His
            115                 120                 125

Asp Tyr Tyr Ile Thr Ser Thr Ser Asn Gly Ser Leu Glu Gly Leu Glu
    130                 135                 140

Asn Arg Glu Gly Gly Val Cys Arg Thr Arg Thr Met Lys Ile Ile Met
145                 150                 155                 160

Lys Val Gly Gln Asp Pro Asn Ala Val Thr Pro Glu Gln Leu Thr Thr
                165                 170                 175

Ser Arg Pro Ser Lys Glu Ala Asp Asn Thr Val Lys Met Ala Thr Gln
            180                 185                 190

Ala Pro Gly Ser Arg Gly Ser Leu Gly Asp Ser Asp Gly Lys His Glu
    195                 200                 205

Thr Val Asn Gln Glu Glu Lys Ser Gly Pro Gly Ala Ser Gly Gly Ser
210                 215                 220

Ser Gly Asp Pro Asp Gly Phe Phe Asn Ser Lys Val Ala Leu Phe Ala
```

```
               225                 230                 235                 240
    Ala Val Gly Ala Gly Cys Val Ile Phe Leu Leu Ile Ile Ile Phe Leu
                    245                 250                 255

Thr Val Leu Leu Leu Lys Leu Arg Lys Arg His Arg Lys His Thr Gln
                    260                 265                 270

Gln Arg Ala Ala Ala Leu Ser Leu Ser Thr Leu Ala Ser Pro Lys Gly
                    275                 280                 285

Gly Ser Gly Thr Ala Gly Thr Glu Pro Ser Asp Ile Ile Ile Pro Leu
                290                 295                 300

Arg Thr Thr Glu Asn Asn Tyr Cys Pro His Tyr Glu Lys Val Ser Gly
    305                 310                 315                 320

Asp Tyr Gly His Pro Val Tyr Ile Val Gln Glu Met Pro Pro Gln Ser
                    325                 330                 335

Pro Ala Asn Ile Tyr Tyr Lys Val
                    340

<210> SEQ ID NO 3
<211> LENGTH: 236
<212> TYPE: PRT
<213> ORGANISM: Artificial Sequence
<220> FEATURE:
<223> OTHER INFORMATION: Synthetic

<400> SEQUENCE: 3

Met Ala Arg Pro Gly Gln Arg Trp Leu Ser Lys Trp Leu Val Ala Met
    1               5                   10                  15

Val Val Leu Thr Leu Cys Arg Leu Ala Thr Pro Leu Ala Lys Asn Leu
                    20                  25                  30

Glu Pro Val Ser Trp Ser Ser Leu Asn Pro Lys Phe Leu Ser Gly Lys
                    35                  40                  45

Gly Leu Val Ile Tyr Pro Lys Ile Gly Asp Lys Leu Asp Ile Ile Cys
                50                  55                  60

Pro Arg Ala Glu Ala Gly Arg Pro Tyr Glu Tyr Tyr Lys Leu Tyr Leu
    65                  70                  75                  80

Val Arg Pro Glu Gln Ala Ala Ala Cys Ser Thr Val Leu Asp Pro Asn
                    85                  90                  95

Val Leu Val Thr Cys Asn Lys Pro His Gln Glu Ile Arg Phe Thr Ile
                    100                 105                 110

Lys Phe Gln Glu Phe Ser Pro Asn Tyr Met Gly Leu Glu Phe Lys Lys
                    115                 120                 125

Tyr His Asp Tyr Tyr Ile Thr Ser Thr Ser Asn Gly Ser Leu Glu Gly
                130                 135                 140

Leu Glu Asn Arg Glu Gly Gly Val Cys Arg Thr Arg Thr Met Lys Ile
    145                 150                 155                 160

Val Met Lys Val Gly Gln Asp Pro Asn Ala Val Thr Pro Glu Gln Leu
                    165                 170                 175

Thr Thr Ser Arg Pro Ser Lys Gly Ser Asp Asn Thr Val Lys Thr Ala
                    180                 185                 190

Thr Gln Ala Pro Gly Arg Gly Ser Gln Gly Asp Ser Asp Gly Lys His
                    195                 200                 205

Glu Thr Val Asn Gln Glu Glu Lys Ser Gly Pro Gly Ala Gly Gly Gly
                    210                 215                 220

Gly Ser Gly Asp Ser Asp Ser Phe Phe Asn Ser Lys
    225                 230                 235
```

```
<210> SEQ ID NO 4
<211> LENGTH: 235
<212> TYPE: PRT
<213> ORGANISM: Artificial Sequence
<220> FEATURE:
<223> OTHER INFORMATION: Synthetic

<400> SEQUENCE: 4
```

Met Ala Arg Pro Gly Gln Arg Trp Leu Gly Lys Trp Leu Val Ala Met
1               5                   10                  15

Val Val Trp Ala Leu Cys Arg Leu Ala Thr Pro Leu Ala Lys Asn Leu
            20                  25                  30

Glu Pro Val Ser Trp Ser Ser Leu Asn Pro Lys Phe Leu Ser Gly Lys
        35                  40                  45

Gly Leu Val Ile Tyr Pro Lys Ile Gly Asp Lys Leu Asp Ile Ile Cys
    50                  55                  60

Pro Arg Ala Glu Arg Pro Tyr Glu Tyr Tyr Lys Leu Tyr Leu Val Arg
65                  70                  75                  80

Pro Glu Gln Ala Ala Ala Cys Ser Thr Val Leu Asp Pro Asn Val Leu
                85                  90                  95

Val Thr Cys Asn Arg Pro Glu Gln Glu Ile Arg Phe Thr Ile Lys Phe
            100                 105                 110

Gln Glu Phe Ser Pro Asn Tyr Met Gly Leu Glu Phe Lys Lys His His
        115                 120                 125

Asp Tyr Tyr Ile Thr Ser Thr Ser Asn Gly Ser Leu Glu Gly Leu Glu
    130                 135                 140

Asn Arg Glu Gly Gly Val Cys Arg Thr Arg Thr Met Lys Ile Ile Met
145                 150                 155                 160

Lys Val Gly Gln Asp Pro Asn Ala Val Thr Pro Glu Gln Leu Thr Thr
                165                 170                 175

Ser Arg Pro Ser Lys Glu Ala Asp Asn Thr Val Lys Met Ala Thr Gln
            180                 185                 190

Ala Pro Gly Ser Arg Gly Ser Leu Gly Asp Ser Asp Gly Lys His Glu
        195                 200                 205

Thr Val Asn Gln Glu Glu Lys Ser Gly Pro Gly Ala Ser Gly Gly Ser
    210                 215                 220

Ser Gly Asp Pro Asp Gly Phe Phe Asn Ser Lys
225                 230                 235

```
<210> SEQ ID NO 5
<211> LENGTH: 221
<212> TYPE: PRT
<213> ORGANISM: Artificial Sequence
<220> FEATURE:
<223> OTHER INFORMATION: Synthetic

<400> SEQUENCE: 5
```

Met Ser Asp Gly Asp Tyr Asp Tyr Leu Ile Lys Phe Leu Ala Leu Gly
1               5                   10                  15

Asp Ser Gly Val Gly Lys Thr Ser Val Leu Tyr Gln Tyr Thr Asp Gly
            20                  25                  30

Lys Phe Asn Ser Lys Phe Ile Thr Thr Val Gly Ile Asp Phe Arg Glu
        35                  40                  45

Lys Arg Val Val Tyr Arg Ala Ser Gly Pro Asp Gly Ala Thr Gly Arg
    50                  55                  60

Gly Gln Arg Ile His Leu Gln Leu Trp Asp Thr Ala Gly Gln Glu Arg
65                  70                  75                  80

```
Phe Arg Ser Leu Thr Thr Ala Phe Phe Arg Asp Ala Met Gly Phe Leu
                85                  90                  95

Leu Leu Phe Asp Leu Thr Asn Glu Gln Ser Phe Leu Asn Val Arg Asn
            100                 105                 110

Trp Ile Ser Gln Leu Gln Met His Ala Tyr Cys Glu Asn Pro Asp Ile
        115                 120                 125

Val Leu Cys Gly Asn Lys Ser Asp Leu Glu Asp Gln Arg Val Val Lys
    130                 135                 140

Glu Glu Glu Ala Ile Ala Leu Ala Glu Lys Tyr Gly Ile Pro Tyr Phe
145                 150                 155                 160

Glu Thr Ser Ala Ala Asn Gly Thr Asn Ile Ser Gln Ala Ile Glu Met
                165                 170                 175

Leu Leu Asp Leu Ile Met Lys Arg Met Glu Arg Cys Val Asp Lys Ser
            180                 185                 190

Trp Ile Pro Glu Gly Val Val Arg Ser Asn Gly His Ala Ser Thr Asp
        195                 200                 205

Gln Leu Ser Glu Glu Lys Glu Lys Gly Ala Cys Gly Cys
    210                 215                 220

<210> SEQ ID NO 6
<211> LENGTH: 221
<212> TYPE: PRT
<213> ORGANISM: Artificial Sequence
<220> FEATURE:
<223> OTHER INFORMATION: Synthetic

<400> SEQUENCE: 6

Met Ser Asp Gly Asp Tyr Asp Tyr Leu Ile Lys Phe Leu Ala Leu Gly
1               5                   10                  15

Asp Ser Gly Val Gly Lys Thr Ser Val Leu Tyr Gln Tyr Thr Asp Gly
            20                  25                  30

Lys Phe Asn Ser Lys Phe Ile Thr Thr Val Gly Ile Asp Phe Arg Glu
        35                  40                  45

Lys Arg Val Val Tyr Arg Ala Asn Gly Pro Asp Gly Ala Val Gly Arg
    50                  55                  60

Gly Gln Arg Ile His Leu Gln Leu Trp Asp Thr Ala Gly Gln Glu Arg
65                  70                  75                  80

Phe Arg Ser Leu Thr Thr Ala Phe Phe Arg Asp Ala Met Gly Phe Leu
                85                  90                  95

Leu Leu Phe Asp Leu Thr Asn Glu Gln Ser Phe Leu Asn Val Arg Asn
            100                 105                 110

Trp Ile Ser Gln Leu Gln Met His Ala Tyr Cys Glu Asn Pro Asp Ile
        115                 120                 125

Val Leu Cys Gly Asn Lys Ser Asp Leu Glu Asp Gln Arg Ala Val Lys
    130                 135                 140

Glu Glu Glu Ala Arg Glu Leu Ala Glu Lys Tyr Gly Ile Pro Tyr Phe
145                 150                 155                 160

Glu Thr Ser Ala Ala Asn Gly Thr Asn Ile Ser His Ala Ile Glu Met
                165                 170                 175

Leu Leu Asp Leu Ile Met Lys Arg Met Glu Arg Cys Val Asp Lys Ser
            180                 185                 190

Trp Ile Pro Glu Gly Val Val Arg Ser Asn Gly His Thr Ser Ala Asp
        195                 200                 205

Gln Leu Ser Glu Glu Lys Glu Lys Gly Leu Cys Gly Cys
    210                 215                 220
```

<210> SEQ ID NO 7
<211> LENGTH: 218
<212> TYPE: PRT
<213> ORGANISM: Artificial Sequence
<220> FEATURE:
<223> OTHER INFORMATION: Synthetic

<400> SEQUENCE: 7

```
Met Thr Asp Gly Asp Tyr Asp Tyr Leu Ile Lys Leu Leu Ala Leu Gly
1               5                   10                  15

Asp Ser Gly Val Gly Lys Thr Thr Phe Leu Tyr Arg Tyr Thr Asp Asn
            20                  25                  30

Lys Phe Asn Pro Lys Phe Ile Thr Thr Val Gly Ile Asp Phe Arg Glu
        35                  40                  45

Lys Arg Val Val Tyr Asn Ala Gln Gly Pro Asn Gly Ser Ser Gly Lys
50                  55                  60

Ala Phe Lys Val His Leu Gln Leu Trp Asp Thr Ala Gly Gln Glu Arg
65                  70                  75                  80

Phe Arg Ser Leu Thr Thr Ala Phe Phe Arg Asp Ala Met Gly Phe Leu
                85                  90                  95

Leu Met Phe Asp Leu Thr Ser Gln Gln Ser Phe Leu Asn Val Arg Asn
            100                 105                 110

Trp Met Ser Gln Leu Gln Ala Asn Ala Tyr Cys Glu Asn Pro Asp Ile
        115                 120                 125

Val Leu Ile Gly Asn Lys Ala Asp Leu Pro Asp Gln Arg Glu Val Asn
130                 135                 140

Glu Arg Gln Ala Arg Glu Leu Ala Asp Lys Tyr Gly Ile Pro Tyr Phe
145                 150                 155                 160

Glu Thr Ser Ala Ala Thr Gly Gln Asn Val Glu Lys Ala Val Glu Thr
                165                 170                 175

Leu Leu Asp Leu Ile Met Lys Arg Met Glu Gln Cys Val Glu Lys Thr
            180                 185                 190

Gln Ile Pro Asp Thr Val Asn Gly Gly Asn Ser Gly Asn Leu Asp Gly
        195                 200                 205

Glu Lys Pro Pro Glu Lys Lys Cys Ile Cys
210                 215
```

<210> SEQ ID NO 8
<211> LENGTH: 218
<212> TYPE: PRT
<213> ORGANISM: Artificial Sequence
<220> FEATURE:
<223> OTHER INFORMATION: Synthetic

<400> SEQUENCE: 8

```
Met Thr Asp Gly Asp Tyr Asp Tyr Leu Ile Lys Leu Leu Ala Leu Gly
1               5                   10                  15

Asp Ser Gly Val Gly Lys Thr Thr Phe Leu Tyr Arg Tyr Thr Asp Asn
            20                  25                  30

Lys Phe Asn Pro Lys Phe Ile Thr Thr Val Gly Ile Asp Phe Arg Glu
        35                  40                  45

Lys Arg Val Val Tyr Asn Ala Asp Thr Gln Gly Ala Asp Gly Ala Ser Gly Lys
50                  55                  60

Ala Phe Lys Val His Leu Gln Leu Trp Asp Thr Ala Gly Gln Glu Arg
65                  70                  75                  80

Phe Arg Ser Leu Thr Thr Ala Phe Phe Arg Asp Ala Met Gly Phe Leu
                85                  90                  95
```

Leu Met Phe Asp Leu Thr Ser Gln Gln Ser Phe Leu Asn Val Arg Asn
            100                 105                 110

Trp Met Ser Gln Leu Gln Ala Asn Ala Tyr Cys Glu Asn Pro Asp Ile
        115                 120                 125

Val Leu Ile Gly Asn Lys Ala Asp Leu Pro Asp Gln Arg Glu Val Asn
    130                 135                 140

Glu Arg Gln Ala Arg Glu Leu Ala Glu Lys Tyr Gly Ile Pro Tyr Phe
145                 150                 155                 160

Glu Thr Ser Ala Ala Thr Gly Gln Asn Val Glu Lys Ser Val Glu Thr
                165                 170                 175

Leu Leu Asp Leu Ile Met Lys Arg Met Glu Lys Cys Val Glu Lys Thr
                180                 185                 190

Gln Val Pro Asp Thr Val Asn Gly Gly Asn Ser Gly Lys Leu Asp Gly
            195                 200                 205

Glu Lys Pro Ala Glu Lys Lys Cys Ala Cys
210                 215

<210> SEQ ID NO 9
<211> LENGTH: 20
<212> TYPE: DNA
<213> ORGANISM: Artificial Sequence
<220> FEATURE:
<223> OTHER INFORMATION: Synthetic

<400> SEQUENCE: 9
atcctgaagt gcattctgcc                                               20

<210> SEQ ID NO 10
<211> LENGTH: 19
<212> TYPE: DNA
<213> ORGANISM: Artificial Sequence
<220> FEATURE:
<223> OTHER INFORMATION: Synthetic

<400> SEQUENCE: 10
tagggtactg agcgagagg                                                19

<210> SEQ ID NO 11
<211> LENGTH: 19
<212> TYPE: DNA
<213> ORGANISM: Artificial Sequence
<220> FEATURE:
<223> OTHER INFORMATION: Synthetic

<400> SEQUENCE: 11
tggccttcac tgtcatagc                                                19

<210> SEQ ID NO 12
<211> LENGTH: 19
<212> TYPE: DNA
<213> ORGANISM: Artificial Sequence
<220> FEATURE:
<223> OTHER INFORMATION: Synthetic

<400> SEQUENCE: 12
ttccaggccc atgtagttg                                                19